US011554007B2

(12) United States Patent
Limem et al.

(10) Patent No.: US 11,554,007 B2
(45) Date of Patent: Jan. 17, 2023

(54) EXPANDABLE ABSORBABLE IMPLANTS FOR BREAST RECONSTRUCTION AND AUGMENTATION

(71) Applicant: Tepha, Inc., Lexington, MA (US)

(72) Inventors: Skander Limem, Lynnfield, MA (US); Bhavin Shah, Lowell, MA (US); Said Rizk, Windham, NH (US); Matthew Dubois, Ayer, MA (US); Simon F. Williams, Cambridge, MA (US)

(73) Assignee: Tepha, Inc., Lexington, MA (US)

( * ) Notice: Subject to any disclaimer, the term of this patent is extended or adjusted under 35 U.S.C. 154(b) by 20 days.

(21) Appl. No.: 16/279,378

(22) Filed: Feb. 19, 2019

(65) Prior Publication Data

US 2019/0254807 A1 Aug. 22, 2019

Related U.S. Application Data

(60) Provisional application No. 62/632,498, filed on Feb. 20, 2018.

(51) Int. Cl.
*A61F 2/12* (2006.01)
*A61F 2/00* (2006.01)
(Continued)

(52) U.S. Cl.
CPC .............. *A61F 2/12* (2013.01); *A61B 90/02* (2016.02); *A61F 2/0063* (2013.01); *A61K 35/35* (2013.01);
(Continued)

(58) Field of Classification Search
CPC .. A61F 2/12; A61F 2/0063; A61F 2250/0031; A61F 2002/006; A61B 90/02; A61L 2430/04
See application file for complete search history.

(56) References Cited

U.S. PATENT DOCUMENTS 6,408,656 B1 6/2002 Ory
8,709,023 B2 4/2014 Shalaby
(Continued)

FOREIGN PATENT DOCUMENTS

| EP | 2002800 A1 * | 12/2008 | ........... A61F 2/0063 |
|---|---|---|---|
| WO | 2006116000 | 11/2006 | |
| WO | 2015006737 | 1/2015 | |

OTHER PUBLICATIONS

Becker, H, et al, "The Use of Synthetic Mesh in Reconstructive, Revision, and Cosmetic Breast Surgery" Aesth Plast Surg (2013) 37:914-921 (Year: 2013).*

(Continued)

*Primary Examiner* — Jennifer Dieterle
*Assistant Examiner* — Rebecca Lynee Zimmerman
(74) *Attorney, Agent, or Firm* — Wolf, Greenfield & Sacks, P.C.

(57) ABSTRACT

Expandable absorbable implants have been developed that are suitable for breast reconstruction following mastectomy. The implants can be implanted in the vicinity of a tissue expander, for example, by suturing to the detached edge of the pectoralis major muscle to function as a pectoralis extender, and used to form a sling for a tissue expander. The implants, which permit tissue-ingrowth and slowly degrade, can be expanded in the breast using a tissue expander in order to form a pocket for a permanent breast implant. After expansion, the tissue expander can be removed and replaced with a permanent breast implant. The expandable implants help reduce patient discomfort resulting from tissue expansion, and avoid the need to use allografts or xenografts to create the pocket for the tissue expander. The expandable absorbable implant preferably comprises poly-4-hydroxybutyrate or copolymer thereof.

31 Claims, 9 Drawing Sheets

(51) Int. Cl.
*A61K 35/35* (2015.01)
*A61L 27/54* (2006.01)
*A61B 90/00* (2016.01)
*A61B 17/00* (2006.01)

(52) U.S. Cl.
CPC ..... *A61L 27/54* (2013.01); *A61B 2017/00969* (2013.01); *A61F 2210/0004* (2013.01); *A61F 2250/0003* (2013.01); *A61F 2250/0004* (2013.01); *A61F 2250/0059* (2013.01); *A61L 2430/04* (2013.01); *A61M 2202/08* (2013.01)

(56) References Cited

U.S. PATENT DOCUMENTS

| | | | |
|---|---|---|---|
| 8,858,629 B2 | 10/2014 | Moses | |
| 9,532,867 B2 | 1/2017 | Felix | |
| 9,566,370 B2 | 2/2017 | Mathisen | |
| 10,085,826 B2 | 10/2018 | Shalaby | |
| 10,098,722 B2 | 10/2018 | Shalaby | |
| 10,702,364 B2 | 7/2020 | Greenhalgh | |
| 10,856,960 B2 | 12/2020 | Shalaby | |
| 2005/0070930 A1* | 3/2005 | Kammerer | A61F 2/0063 606/151 |
| 2007/0282160 A1* | 12/2007 | Sheu | A61L 31/148 600/30 |
| 2010/0023029 A1 | 1/2010 | Young | |
| 2012/0022646 A1 | 1/2012 | Mortarino | |
| 2012/0184974 A1* | 7/2012 | Becker | A61L 31/148 606/151 |
| 2012/0226352 A1 | 9/2012 | Becker | |
| 2013/0267137 A1* | 10/2013 | Peniston | A61F 2/0063 442/50 |
| 2014/0081296 A1 | 3/2014 | Palmer | |
| 2015/0088171 A1* | 3/2015 | Mathisen | D04B 21/12 606/151 |
| 2015/0313700 A1* | 11/2015 | Rizk | A61F 2/0063 606/151 |
| 2019/0008623 A1* | 1/2019 | Nemoto | A61L 27/48 |
| 2021/0128288 A1 | 5/2021 | Shalaby | |

OTHER PUBLICATIONS

International Search Report for corresponding application PCT/US2019/018543 dated Jun. 11, 2019.

Bertozzi, et al., "Tissue expansion for breast reconstruction: Methods and techniques", Ann Med Surg. 21:34-44 (2017).

Jewell, et al. "The development of SERI Surgical Scaffold, an engineered biological scaffold", Ann. of N.Y. Acad. Sci., 1358:44-55 (2015).

Williams, et al., "Poly-4-hydroxybutyrate (P4HB): a new generation of resorbable medical devices for tissue repair and regeneration", Biomed. Tech., 58(5):439-52 (2013).

\* cited by examiner

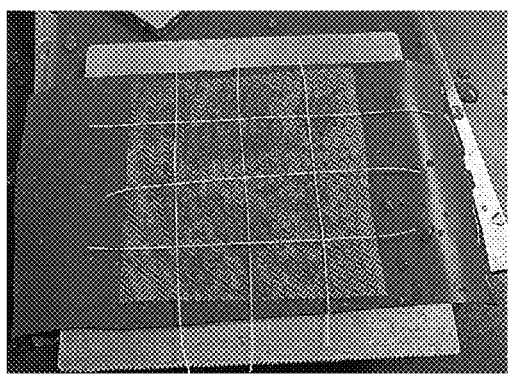
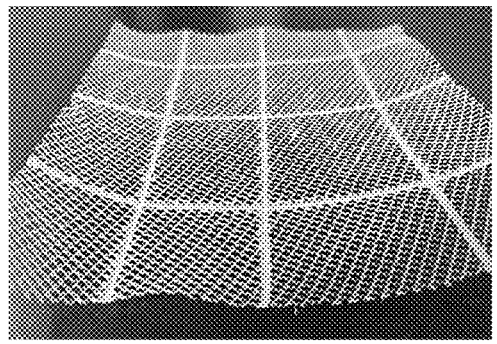
FIG. 4A                    FIG. 4B

EXPANDABLE ABSORBABLE IMPLANTS FOR BREAST RECONSTRUCTION AND AUGMENTATION

CROSS-REFERENCE TO RELATED APPLICATIONS

This application claims the benefit of and priority to U.S. Application No. 62/632,498, filed on Feb. 20, 2018, which is hereby incorporated herein by reference in its entirety.

FIELD OF THE INVENTION

The present invention generally relates to the field of surgery, and more particularly, the invention relates to expandable absorbable implants that can be used in conjunction with tissue expanders in breast reconstruction and breast augmentation. The expandable implant can be implanted in the vicinity of a tissue expander in the breast, expanded upon inflation of the tissue expander, and allows tissue in-growth into the implant as the implant degrades. After expansion, the tissue expander may be removed from the breast, and replaced with a permanent breast implant. The implants are suitable for use in patients that have elected breast reconstruction following a mastectomy.

BACKGROUND OF THE INVENTION

Breast reconstruction following mastectomy has become an integral and important part of breast cancer treatment with the surgery providing the patient with both aesthetic and psychosocial benefits. Nearly 65% of US breast reconstruction procedures now use a tissue expander (TE) which is temporarily implanted in the breast to create a pocket for a permanent breast implant in the first step of the procedure. The TE is then removed and replaced with a permanent breast implant in a second step. In the first step of the reconstruction procedure, the pectoralis major muscle and serratus anterior muscle are released, elevated, and used to cover the TE. The TE may then be expanded by injecting liquid or gas into the device. Expansion is normally started 10 to 14 days after implantation of the TE, and repeated every 1-4 weeks. The TE is often filled with up to 50% of the final volume intraoperatively. Typically, 60-120 cm$^3$ of saline is injected into the TE each time thereafter, and expansion is usually completed within 2 months.

A more recent modification of the TE breast reconstruction procedure is to use an acellular dermal matrix (ADM) to help cover the TE (Bertozzi, N. *Ann Med Surg.* 21:34-44 (2017)). In a typical procedure, the pectoralis major muscle is mobilized, and the ADM is attached to the edge of the muscle in order to create a sling and submuscular pocket for the TE. The use of ADM eliminates the need to release and elevate the serratus anterior muscle, the pectoralis minor muscle, and the rectus abdominis fascia, and consequently, reduces postoperative pain. Other advantages of using an ADM include (i) creation of a larger pocket size, (ii) the ability to use a larger intraoperative fill volume for the TE and more rapid expansion, (iii) reduced incidence of capsular contracture formation, and (iv) improvements in aesthetic results, including a more natural shape and better definition of the lower pole.

While the use of ADM materials has many advantages, there are a number of significant disadvantages to their use. First, ADM resists stretching which puts undue stress on the pectoralis major muscle, and can be uncomfortable for the patient. Second, ADM tends to be very expensive. And, third, ADM is an animal or human derived implant with an associated risk of disease transmission.

A few researchers have sought alternatives to using an ADM as a pectoralis extender. US Patent Application No. 20120022646 to Mortarino and Altman discloses a method of using a silk scaffold device in two-stage breast reconstruction. The scaffolds, now known as SERI® Surgical Scaffold, however, were designed to preserve mechanical stability, for example, using a "node-lock" design, and therefore were not designed to expand when sutured in place, and the TE inflated. As reported by Jewell et al. *Ann. N.Y. Acad. Sci.* 1358:44-55 (2015), the silk scaffolds have only a 7% elongation to break in the transverse direction and approximately a 4% elongation to break in the vertical direction which means that these scaffolds will resist expansion as the TE is expanded.

U.S. Pat. No. 8,858,629 to Moses discloses systems and methods for mastopexy (breast lift procedures), including TephaFLEX™ mesh, made from Tepha's P4HB™ polymer (poly-4-hydroxybutyrate polymer), but does not disclose an expandable mesh made from P4HB suitable for use with a TE in breast reconstruction. Instead, a highly oriented P4HB mesh is disclosed that is designed to support the breast in a breast lift procedure, and not stretch after implantation (since stretching would result in ptosis).

U.S. Pat. No. 9,532,867 to Felix discloses absorbable implants for breast surgery that confer shape to the breast, and that cannot stretch more than 30% of their original length. The implants are designed to support the breast following surgery to prevent ptosis, and are not designed for use with a TE for breast reconstruction.

U.S. Pat. No. 9,566,370 to Mathisen discloses a mesh implant, for reconstruction of soft tissue defects, made from a first and second material, wherein the second material is degraded at a later point in time than the first material following implantation. The mesh is described as having a very low elongation during the initial wound healing period, and was not designed for use with a TE for breast reconstruction.

An absorbable implant that can (i) be attached to the edge of the pectoralis major muscle in order to create a sling and submuscular pocket for a TE, (ii) expand when the TE is inflated, (iii) allow tissue ingrowth, and (iv) degrade in vivo, would be particularly desirable. Ideally, the implant minimizes the stress on the pectoralis major muscle during inflation of the TE, and thereby reduces patient discomfort during, and subsequent to, inflation. The absorbable implant should preferably be capable of continued expansion as the TE is inflated so that the pectoralis major muscle is not stretched. The implant may optionally have a tensile strength that initially increases when the TE is inflated. The implant may comprise a polymer that is unoriented or partially oriented, and that becomes more oriented after implantation upon expansion of the TE. The implant should have sufficient integrity to cover the TE expander, form a sling and submuscular pocket for the TE, and remodel in vivo so that a breast implant can be placed in the pocket when the TE is removed. The implant should be porous in order to allow tissue ingrowth, preferably with average pore diameters of at least 75 µm. And preferably, the implant should be completely degraded in two years, and replaced with new tissue. In order to allow expansion of the implant when the TE is inflated, the implant may comprise sacrificial and non-sacrificial elements, such as fibers and struts, wherein the sacrificial elements degrade faster than the non-sacrificial elements, or yield (i.e. stretch) when placed under tension by inflation of the tissue expander. If the implant comprises sacrificial and non-sacrificial elements, it would be desirable for the implant to have a strength retention that is at least 40% of its original tensile strength or burst strength three months after implantation. In order to reduce the risk of disease transmission, the implant would preferably be made synthetically or biosynthetically.

It is therefore an object of the invention to provide an implant for use in the vicinity of a TE in the breast that is absorbable and expandable.

It is another object of the invention to provide methods to prepare an absorbable expandable implant for use in the vicinity of a TE in the breast.

It is still another objection of the invention to provide methods to implant an absorbable expandable implant in the vicinity of a TE in the breast.

SUMMARY OF THE INVENTION

Implants that are absorbable and expandable have been developed that are suitable for use in breast reconstruction and breast augmentation. The implants may be placed in the vicinity of a TE, and are preferably attached to the mobilized and elevated pectoralis major muscle to create a sling that can form a submuscular pocket for a TE. The implants are porous and made with polymeric materials, and expand when the TE is inflated to make an enlarged pocket for a permanent breast implant. The implants can expand in one or more directions, including uniaxial and biaxial expansion. The implants can be expanded in one or more directions between 31% and 100% of their original dimensions, more preferably between 35% and 75% of their original dimensions, and even more preferably between 45% and 65% of their original dimensions. The implants may optionally become stronger upon initial inflation of the TE. The implants may comprise sacrificial and non-sacrificial elements that allow the implants to expand as the TE is inflated. Following implantation, the implants are designed to remodel and be replaced with in-growing tissue as they degrade. The implants allow the TE to be removed once expansion is completed, and the remodeling implant can then be used to help cover a permanent breast implant. The implants reduce the stress placed on the pectoralis major muscle, and associated patient discomfort, which occurs in current procedures using a TE to create a submuscular pocket for a breast implant. The implants also eliminate the need to release and elevate the serratus anterior muscle, the pectoralis minor muscle, and the rectus abdominis fascia, and consequently reduce postoperative pain related to these procedures. The use of the implants instead of ADM materials decreases the short-term and long-term risks of infection because the implants are derived from synthetic sources, and are completely absorbed in vivo.

Methods to prepare the implants are also described. The implants are preferably made with absorbable polymers, most preferably with poly-4-hydroxybutyrate and copolymers thereof. The implants preferably comprise unoriented polymers or partially oriented polymers that will stretch as the TE is inflated. The implants may also comprise sacrificial elements that allow the implant to expand when the TE is inflated.

Also disclosed is a method of using the implants with a TE. The method includes mobilizing the pectoralis major muscle, attaching the implant to the elevated pectoralis major muscle to create a submuscular pocket for a TE, inflating the TE, removing the TE, and replacing it with a permanent breast implant.

BRIEF DESCRIPTION OF THE DRAWINGS

FIG. 4(a) is a picture showing a grid of unoriented P4HB extrudate placed on an oriented diamond knitted P4HB mesh that is lying on a silicone pad prior to molding into an expandable absorbable implant for breast reconstruction. FIG. 4(b) is a picture of an expandable absorbable implant for breast reconstruction made from molding a grid of unoriented P4HB extrudate to a diamond knitted P4HB mesh.

DETAILED DESCRIPTION OF THE INVENTION

Figure 1:
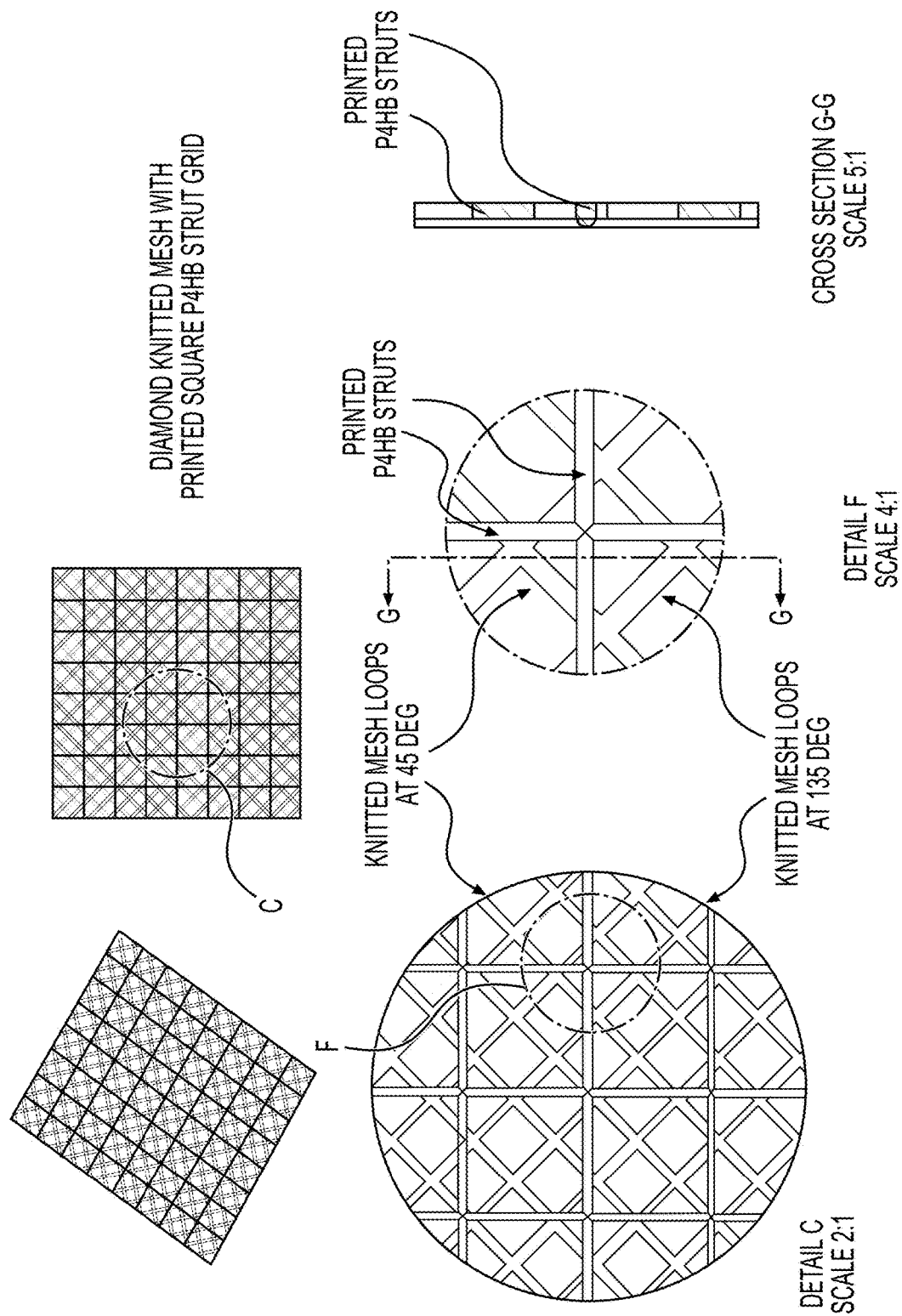
FIG. 1 is a diagram showing an expandable absorbable implant comprising an unoriented square lattice of P4HB struts that have been deposited over a knitted mesh made from oriented P4HB monofilament fiber with the deposited lattice placed at a 45° angle to the mesh loops.
Figure 2:
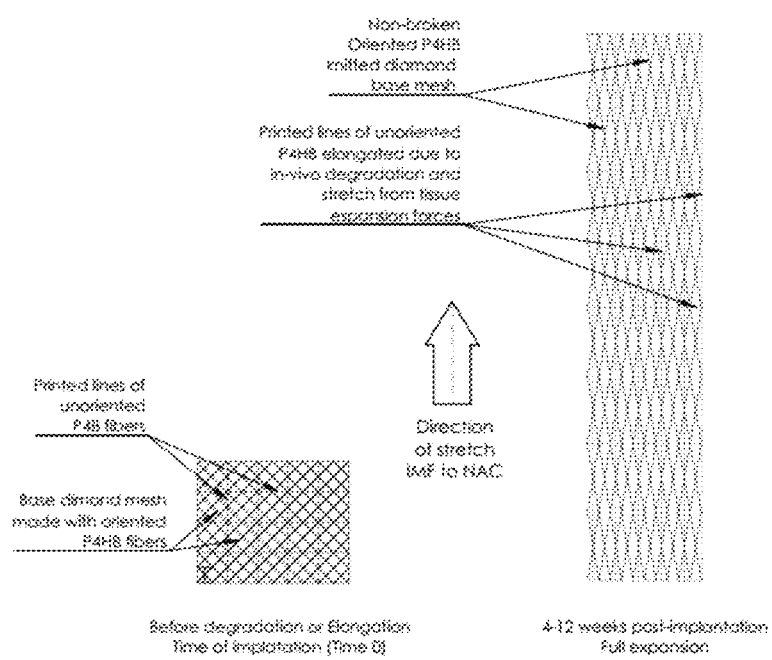
FIG. 2 is a diagram showing how the expandable absorbable implant shown in FIG. 1 can be expanded with a tissue expander after implantation in the breast with the struts stretching and breaking after implantation.

It would be desirable to have an expandable absorbable implant that the surgeon can use in close proximity to a TE to create a submuscular pocket for a breast implant during breast reconstruction and breast augmentation. Ideally, the expandable absorbable implant can be used by mobilizing the pectoralis major muscle, elevating the muscle, attaching the expandable absorbable implant to the edge of the muscle, and using the extended pectoralis-implant structure as a sling to form a submuscular pocket for a TE. The use of the implant in this manner is particularly desirable because it will reduce the stress on the pectoralis major muscle during, and subsequent to, inflation of the TE, by expanding as the TE is inflated, and thereby reduce patient discomfort. The use of the implant will also eliminate the need to release and elevate the serratus anterior muscle, the pectoralis minor muscle, and the rectus abdominis fascia, which can result in increased post-operative pain and increased operating time. Furthermore, it would be highly desirable for the implant to be porous and allow tissue in-growth, degrade in a controlled manner, be replaced over time with the patient's own tissue, and be made from synthetic polymeric material to reduce the risk of disease transmission associated with human or animal-derived implants.

I. Definitions

"Absorbable" as generally used herein means the material is degraded in the body, and the degradation products are eliminated or excreted from the body. The terms "absorbable", "resorbable", "degradable", and "erodible", with or without the prefix "bio", can be used interchangeably herein, to describe materials broken down and gradually absorbed, excreted, or eliminated by the body, whether degradation is due mainly to hydrolysis or mediated by metabolic processes.

"Average pore size diameter" as used herein is calculated using open source ImageJ software available at https://imagej.nih.gov/ij/index.html.

"Bioactive agent" is used herein to refer to therapeutic, prophylactic or diagnostic agents, preferably agents that promote healing and the regeneration of host tissue, and also therapeutic agents that prevent, inhibit or eliminate infection. "Agent" includes a single such agent and is also intended to include a plurality.

"Biocompatible" as generally used herein means the biological response to the material or device being appropriate for the device's intended application in vivo. Any metabolites of these materials should also be biocompatible.

"Blend" as generally used herein means a physical combination of different polymers, as opposed to a copolymer formed of two or more different monomers.

"Breast implant" as used herein refers to a prosthesis that is implanted in place of a female breast, but can also be implanted to change the size, shape and contour of a woman's breast. A "breast implant" is a permanent implant whereas an "absorbable expandable implant" for breast reconstruction is a transitory implant used in conjunction with a tissue expander (TE) to make a pocket suitable for receiving a breast implant.

"Burst strength" as used herein is determined by test method ASTM D6797-02 "Standard test method for bursting strength of fabrics constant rate of extension (CRE) ball burst test," using a MTS Q-Test Elite universal testing machine or similar device. The testing fixture uses a ⅜ inch diameter ball.

"Copolymers of poly-4-hydroxybutyrate" as generally used herein means any polymer containing 4-hydroxybutyrate with one or more different hydroxy acid units.

"Elongation to break" as used herein means the increase in length of a material that occurs when tension is applied to break the material. It is expressed as a percentage of the material's original length.

"Endotoxin units" as used herein are determined using the limulus amebocyte lysate (LAL) assay as further described by Gorbet et al. Biomaterials, 26:6811-6817 (2005).

"Expandable" as generally applied to an implant herein means that the implant can be stretched in one or more directions, including uniaxially or biaxially. The percent expansion of an implant is calculated using the formula:

% expansion=(dimension of implant after expansion−dimension of implant prior to expansion)/dimension of implant prior to expansion.

"Macro-porous" materials or structures as used herein have average pore size diameters of at least 75 microns.

"Molecular weight" as used herein, unless otherwise specified, refers to the weight average molecular weight (Mw), not the number average molecular weight (Mn), and is measured by GPC relative to polystyrene.

"Oriented" as generally used herein refers to molecular alignment of polymer chains in a material. A polymer that has been stretched becomes partly oriented and then highly oriented, and the tensile strength increases with increasing orientation. For example, an unoriented polymeric fiber may be stretched to orient the fiber which results in a polymeric fiber with higher tensile strength. An "oriented mesh" means a mesh made with oriented fibers.

"Orientation ratio" as used herein is the ratio of the output speed to the input speed of two godets (or rollers) used to orient fiber. For example, the orientation ratio would be 3 if the output speed of the fiber is 6 meters per minute, and the input speed of the fiber is 2 meters per minute.

"Poly-4-hydroxybutyrate" as generally used herein means a homopolymer containing 4-hydroxybutyrate units. It can be referred to herein as Tepha's P4HB™ polymer or TephaFLEX® biomaterial (manufactured by Tepha, Inc., Lexington, Mass.).

"Sacrificial polymeric fiber or strut" as generally used herein means an element or component of the implant that is present initially in the implant, but degrades, yields, or breaks in vivo prior to the degradation, stretching, or breakage of a non-sacrificial polymeric fiber or strut. A sacrificial polymeric fiber or strut can initially enhance the strength or stability of the implant, but then is degraded, stretched, or broken in order to allow the implant to expand in vivo. A "non-sacrificial polymeric fiber or strut" as generally used herein means an element or component of the implant that retains strength in vivo longer than a sacrificial polymeric fiber or strut, however, the non-sacrificial polymeric fiber or strut may eventually be broken, stretched or completely degraded after implantation.

"Strength retention" as used herein means the amount of time that a material maintains a particular mechanical property following implantation or exposure to a particular set of conditions. For example, if the stress required to break a multifilament yarn or monofilament fiber after one month is half of its original value then the multifilament or monofilament fiber is said to have a 50% strength retention after one month.

"Suture pullout strength" as used herein means the peak load (kg) at which an implant fails to retain a suture. It is determined using a tensile testing machine by securing an implant in a horizontal plate, threading a suture in a loop through the implant at a distance of 1 cm from the edge of the implant, and securing the suture arms in a fiber grip positioned above the implant. Testing is performed at a crosshead rate of 100 mm/min, and the peak load (kg) is recorded. The suture is selected so that the implant will fail before the suture fails. The suture pullout strength may be converted and expressed as Newtons.

"Tensile modulus" is the ratio of stress to strain for a given material within its proportional limit.

"Tissue expander" ("TE") as used herein means an inflatable breast implant that is placed temporarily in the breast to expand tissues and make room for a breast implant. The TE is expanded periodically, for example, by injecting a fluid or gas into the TE. The TE is removed once the tissue has been sufficiently stretched to make room for a permanent breast implant.

II. Materials for Preparing Absorbable Expandable Implants

Absorbable expandable implants have been developed. The implants are porous, expandable, allow tissue in-growth, and are replaced over time with the patient's own tissues. The dimensions of the implants can be tailored to the individual patient's needs. The implants are preferably made of absorbable polymers with a tunable rate of degradation. The implants may be made from a single component, such as an unoriented, partially or fully oriented monofilament fiber, or from two or more components, such as fibers with different properties or struts with different properties, or combinations thereof. The implants can optionally comprise bioactive agents, as well as cells, including stem cells. The implants so formed preferably have a pyrogen level of less than 20 endotoxin units per device.

A. Polymers for Preparing Absorbable Expandable Implants

The absorbable expandable implants may comprise degradable materials, and more preferably are made completely from degradable materials. In a preferred embodiment, the implants are made from one or more absorbable polymers, preferably absorbable thermoplastic polymers and copolymers. The implant may, for example, be prepared from polymers including, but not limited to, polymers of glycolic acid, lactic acid, 1,4-dioxanone, trimethylene carbonate, 3-hydroxybutyric acid, 4-hydroxybutyrate, ε-caprolactone, including polyglycolic acid, polylactic acid, polydioxanone, polycaprolactone, copolymers of glycolic and lactic acids, such as VICRYL® polymer, MAXON® and MONOCRYL® polymers, and including poly(lactide-co-caprolactones); poly(orthoesters); polyanhydrides; poly(phosphazenes); polyhydroxyalkanoates; synthetically or biologically prepared polyesters; polycarbonates; tyrosine polycarbonates; polyamides (including synthetic and natural polyamides, polypeptides, and poly(amino acids)); polyesteramides; poly(alkylene alkylates); polyethers (such as polyethylene glycol, PEG, and polyethylene oxide, PEO); polyvinyl pyrrolidones or PVP; polyurethanes; polyetheresters; polyacetals; polycyanoacrylates; poly(oxyethylene)/poly(oxypropylene) copolymers; polyacetals, polyketals; polyphosphates; (phosphorous-containing) polymers; polyphosphoesters; polyalkylene oxalates; polyalkylene succinates; poly(maleic acids); silk (including recombinant silks and silk derivatives and analogs); chitin; chitosan; modified chitosan; biocompatible polysaccharides; hydrophilic or water soluble polymers, such as polyethylene glycol, (PEG) or polyvinyl pyrrolidone (PVP), with blocks of other biocompatible or biodegradable polymers, for example, poly(lactide), poly(lactide-co-glycolide, or polycaprolactone and copolymers thereof, including random copolymers and block copolymers thereof. Preferably the absorbable polymer or copolymer will be substantially or completely resorbed two years after implantation.

Blends of polymers, preferably absorbable polymers, can also be used to prepare the absorbable expandable implants. Particularly preferred blends of absorbable polymers include, but are not limited to, polymers of glycolic acid, lactic acid, 1,4-dioxanone, trimethylene carbonate, 3-hydroxybutyric acid, 4-hydroxybutyric acid, ε-caprolactone or copolymers thereof.

In a particularly preferred embodiment, the absorbable expandable implants comprise poly-4-hydroxybutyrate (Tepha's P4HB™ polymer, Lexington, Mass.) or a copolymer thereof, and can be made completely with P4HB or copolymer thereof. Copolymers include P4HB with another hydroxyacid, such as 3-hydroxybutyrate, and P4HB with glycolic acid or lactic acid monomer. P4HB is a strong, pliable thermoplastic polyester that is biocompatible and resorbable (Williams, et al. Poly-4-hydroxybutyrate (P4HB): a new generation of resorbable medical devices for tissue repair and regeneration, Biomed. Tech. 58(5):439-452 (2013)). Upon implantation, P4HB hydrolyzes to its monomer, and the monomer is metabolized via the Krebs cycle to carbon dioxide and water. In a preferred embodiment, the P4HB homopolymer and copolymers thereof have a weight average molecular weight, Mw, within the range of 50 kDa to 1,200 kDa (by GPC relative to polystyrene) and more preferably from 100 kDa to 600 kDa. A weight average molecular weight of the polymer of 50 kDa or higher is preferred for processing and mechanical properties.

B. Additives

Certain additives may be incorporated into the implant, preferably in the absorbable polymer, copolymer or blends thereof that are used to make the implant. Preferably, these additives are incorporated during a compounding process to produce pellets that can be subsequently melt-processed. For example, pellets may be extruded into fibers suitable for making the implants. In another embodiment, the additives may be incorporated using a solution-based process, for example, fibers may be spun from solutions of the polymer and one or more additives. In a preferred embodiment, the additives are biocompatible, and even more preferably the additives are both biocompatible and resorbable.

In one embodiment, the additives may be nucleating agents and/or plasticizers. These additives may be added in sufficient quantity to produce the desired result. In general, these additives may be added in amounts between 1% and 20% by weight. Nucleating agents may be incorporated to increase the rate of crystallization of the polymer, copolymer or blend. Such agents may be used, for example, to facilitate fabrication of the implant, and to improve the mechanical properties of the implant. Preferred nucleating agents include, but are not limited to, salts of organic acids such as calcium citrate, polymers or oligomers of PHA polymers and copolymers, high melting polymers such as PGA, talc, micronized mica, calcium carbonate, ammonium chloride, and aromatic amino acids such as tyrosine and phenylalanine.

Plasticizers that may be incorporated into the compositions for preparing the implants include, but are not limited to, di-n-butyl maleate, methyl laureate, dibutyl fumarate, di(2-ethylhexyl) (dioctyl) maleate, paraffin, dodecanol, olive oil, soybean oil, polytetramethylene glycols, methyl oleate, n-propyl oleate, tetrahydrofurfuryl oleate, epoxidized linseed oil, 2-ethyl hexyl epoxytallate, glycerol triacetate, methyl linoleate, dibutyl fumarate, methyl acetyl ricinoleate, acetyl tri(n-butyl) citrate, acetyl triethyl citrate, tri(n-butyl) citrate, triethyl citrate, bis(2-hydroxyethyl) dimerate, butyl ricinoleate, glyceryl tri-(acetyl ricinoleate), methyl ricinoleate, n-butyl acetyl ricinoleate, propylene glycol ricinoleate, diethyl succinate, diisobutyl adipate, dimethyl azelate, di(n-hexyl) azelate, tri-butyl phosphate, and mixtures thereof. Particularly preferred plasticizers are citrate esters.

C. Bioactive Agents

The implants can be loaded or coated with bioactive agents. Bioactive agents may be included in the implants for a variety of reasons. For example, bioactive agents may be included in order to improve tissue in-growth into the implant, to improve tissue maturation, to provide for the delivery of an active agent, to improve wettability of the implant, to prevent infection, and to improve cell attachment. The bioactive agents may also be incorporated into or onto the structure of the implant.

The implants may contain cellular adhesion factors, including cell adhesion polypeptides. As used herein, the term "cell adhesion polypeptides" refers to compounds having at least two amino acids per molecule that are capable of binding cells via cell surface molecules. The cell adhesion polypeptides include any of the proteins of the extracellular matrix which are known to play a role in cell adhesion, including fibronectin, vitronectin, laminin, elastin, fibrinogen, collagen types I, II, and V, as well as synthetic peptides with similar cell adhesion properties. The cell adhesion polypeptides also include peptides derived from any of the aforementioned proteins, including fragments or sequences containing the binding domains.

The implants can incorporate wetting agents designed to improve the wettability of the surfaces of the implant structures to allow fluids to be easily adsorbed onto the implant surfaces, and to promote cell attachment and or modify the water contact angle of the implant surface. Examples of wetting agents include polymers of ethylene oxide and propylene oxide, such as polyethylene oxide, polypropylene oxide, or copolymers of these, such as PLURONICS®. Other suitable wetting agents include surfactants or emulsifiers.

The implants can contain gels, hydrogels or living hydrogel hybrids to further improve wetting properties and to promote cellular growth throughout the thickness of the scaffold. Hydrogel hybrids consist of living cells encapsulated in a biocompatible hydrogel like gelatin, silk gels, and hyaluronic acid (HA) gels.

The implants can contain active agents designed to stimulate cell in-growth, including growth factors, cellular differentiating factors, cellular recruiting factors, cell receptors, cell-binding factors, cell signaling molecules, such as cytokines, and molecules to promote cell migration, cell division, cell proliferation and extracellular matrix deposition. Such active agents include fibroblast growth factor (FGF), transforming growth factor (TGF), platelet derived growth factor (PDGF), epidermal growth factor (EGF), granulocyte-macrophage colony stimulation factor (GMCSF), vascular endothelial growth factor (VEGF), insulin-like growth factor (IGF), hepatocyte growth factor (HGF), interleukin-1-B (IL-1 B), interleukin-8 (IL-8), and nerve growth factor (NGF), and combinations thereof.

Other bioactive agents that can be incorporated in the implants include antimicrobial agents, in particular antibiotics, disinfectants, oncological agents, anti-scarring agents, anti-inflammatory agents, anesthetics, small molecule drugs, anti-angiogenic factors and pro-angiogenic factors, immunomodulatory agents, and blood clotting agents. The bioactive agents may be proteins such as collagen and antibodies, peptides, polysaccharides such as chitosan, alginate, hyaluronic acid and derivatives thereof, nucleic acid molecules, small molecular weight compounds such as steroids, inorganic materials such as hydroxyapatite, or complex mixtures such as platelet rich plasma. Suitable antimicrobial agents include: bacitracin, biguanide, trichlosan, gentamicin, minocycline, rifampin, vancomycin, cephalosporins, copper, zinc, silver, and gold. Nucleic acid molecules may include DNA, RNA, siRNA, miRNA, antisense or aptamers.

The implants may also contain allograft material and xenograft materials, including acellular dermal matrix material and small intestinal submucosa (SIS).

In yet another preferred embodiment, the implants may incorporate systems for the controlled release of the therapeutic or prophylactic agents.

D. Fibers

The implants may comprise fibers. The fibers are made from degradable thermoplastic polymers, and even more preferably from degradable thermoplastic polyesters. The fibers are preferably made from the degradable materials listed in section II.A above. The fibers may be monofilament fibers, multifilament fibers, or combinations thereof. The fibers may be unoriented, partially oriented, highly oriented or combinations thereof. The fibers may have elongation to break values of 3% to 1,100%. The fibers may have diameters ranging from 1 micron to 5 mm, more preferably from 10 microns to 1 mm, and even more preferably from 20 microns to 750 microns. The fibers may have different weight average molecular weights. The fibers may have different tensile strengths. The fibers may have short strength retention profiles, prolonged strength retention profiles, or combinations thereof. In one embodiment, a short strength retention profile is 1 to 12 weeks, and a prolonged strength retention profile is 4 months to 5 years, more preferably 4 months to 2 years. The fibers may have different degradation rates in vivo. Some fibers may degrade quickly while other fibers may degrade slowly.

Sacrificial fibers that are used to prepare the implants typically have one or more of the following properties: an elongation to break of 100-1,000%; a tensile strength of 50-300 MPa, a tensile modulus of 70-400 MPa, and an average fiber diameter of 10 microns to 500 microns. Non-sacrificial fibers that are used to prepare the implants typically have one or more of the following properties: an elongation to break of 10-100%; a tensile strength of 301-1,300 MPa, a tensile modulus of 401 MPa-1 GPa, and an average fiber diameter of 10 microns to 1 mm. Sacrificial fibers used to prepare the implants will typically yield or stretch upon inflation of the TE before the non-sacrificial fibers yield or stretch in the implant.

Implants that can be expanded in vivo with a tissue expander can be prepared from the fibers described above. Such implants can be produced from slow and fast degrading fibers, degradable fibers of different molecular weights, fibers that yield or stretch differently under tension either relative to other fibers or relative to other components of the implants such as struts, fibers of different tensile strengths, fibers that are unoriented, partially oriented and fully oriented, fibers with different elongation to break values, or combinations thereof.

E. Struts

The implants may comprise struts. The struts are made from degradable thermoplastic polymers, and even more preferably from degradable thermoplastic polyesters. The struts are preferably made from the degradable materials listed in section II.A above. The struts typically have a width or average diameter between 1 micron and 5 mm, more preferably between 10 microns and 1 mm, and even more preferably from 20 microns to 750 microns. The struts are preferably unoriented, but may be partially or highly oriented. The struts may have elongation to break values of 3% to 1,100%. The struts in the implants may have different weight average molecular weights. The struts may have different tensile strengths. The struts may have short strength retention profiles, prolonged strength retention profiles, or combinations thereof. In one embodiment, a short strength retention profile is 1 to 12 weeks, and a prolonged strength retention profile is 4 months to 5 years, more preferably 4 months to 2 years. The struts in an implant may have different degradation rates in vivo. Some struts may degrade quickly while other struts may degrade slowly.

Sacrificial struts that are used to prepare the implants typically have one or more of the following properties: an elongation to break of 100-1,000%; a tensile strength of 50-300 MPa, a tensile modulus of 70-400 MPa, and an average strut width of 10-500 microns. Non-sacrificial struts that are used to prepare the implants typically have one or more of the following properties: an elongation to break of 10-100%; a tensile strength of 301-1,300 MPa, a tensile modulus of 401 MPa-1 GPa, and an average strut width of 50-500 microns.

Implants that can be expanded in vivo with a tissue expander can be prepared with the struts described above. Such implants can be produced from slow and fast degrading struts, degradable struts of different molecular weights, struts of different tensile strengths, struts that yield or stretch differently under tension either relative to other struts or relative to other components of the implant such as fibers, struts that are unoriented, partially oriented and fully oriented, struts with different elongation to break values, or combinations thereof.

III. Methods of Manufacturing Absorbable Expandable Breast Implants

A variety of methods can be used to manufacture the implants.

A. Implants with Absorbable Fibers and Meshes

The expandable absorbable implants may comprise the fibers disclosed herein. The fibers described herein may be processed into meshes, for example, by knitting, weaving, or crocheting. A particularly preferred mesh for use in preparing the expandable implants is a warp knit mesh. The expandable meshes described herein may contain slow degrading fibers, fast degrading fibers, degradable fibers of different weight average molecular weights, fibers of different tensile strengths, fibers that yield (or stretch) under different tensions, fibers of different diameters, fibers that are unoriented, partially oriented and fully oriented, fibers with different elongation to break values, or any combinations thereof.

In one preferred embodiment, the implants comprise fibers made from P4HB, and more preferably from P4HB monofilament fiber. The P4HB monofilament fiber may be unoriented, partially oriented (i.e. partially stretched after extrusion) or fully oriented. In one embodiment, P4HB monofilament fiber may be produced according to the following method. Bulk P4HB resin in pellet form is dried to under 300 ppm water content using a rotary vane vacuum pump system. The dried resin is transferred to an extruder feed hopper with nitrogen purge to keep the pellets dry. The pellets are gravity fed into a chilled feeder section and introduced into an extruder barrel, with a 1.5 inch (3.8 cm) diameter, and fitted with an extrusion screw with a 30:1 L/D ratio. The extruder barrel preferably contains 5 heating zones (or extrusion zones)—zones 1, 2, 3, 4 and 5, and is manufactured by American Kuhne. The heated and softened resin from the extruder is fed into a heated metering pump (melt pump) and from the melt pump the extruded resin is fed into the heated block and an 8-hole spinneret assembly. Processing profile ranges from 40° C. to 260° C. for temperatures, and 400 psi to 2000 psi for pressures. The molten filaments are preferably water quenched and optionally conveyed into a one to three-stage orientation line, optionally with inline relaxation, before winding of the monofilaments on spools. This procedure may, for example, be used to produce P4HB fibers with one or more of the following properties: an elongation to break from 10-1,000%, a tensile strength from 50-1,300 MPa, and a tensile modulus from 70-1,000 MPa. The P4HB fibers may have average diameters ranging from 10 microns to 1 mm. The P4HB fibers may have short or long strength retention profiles. For example, their strength retention profiles in vivo may be 1 to 12 weeks or 4 months to 2 years.

Expandable absorbable implants comprising knitted meshes may be produced using P4HB fibers. A suitable knitted P4HB mesh may be prepared, for example, by the following method. Monofilament fibers from 49 spools are pulled under uniform tension to the surface of a warp beam. A warp is a large wide spool onto which individual fibers are wound in parallel to provide a sheet of fibers ready for coating with a 10% solution of Tween® 20 lubricant. Tween® 20 lubricant is added to the surface of the sheet of fiber by means of a 'kiss' roller that is spinning and is immersed in a bath filled with Tween® 20. The upper surface of the roller is brought into contact with the sheet of fiber, and the roller spun at a uniform speed to provide a consistent application of Tween® 20 finish. Following the application of Tween® 20, the sheet of fiber is placed onto a creel position such that each spooled fiber is aligned and wrapped side by side to the next spooled fiber on a warp beam. Next, warp beams are converted into a finished mesh fabric by means of interlocking knit loops. Eight warp beams are mounted in parallel onto a tricot machine let-offs and fed into the knitting elements at a constant rate determined by the 'runner length'. Each individual monofilament fiber from each beam is fed through a series of dynamic tension elements down into the knitting 'guides'. Each fiber is passed through a single guide, which is fixed to a guide bar. The guide bar directs the fibers around the needles forming the mesh structure. The mesh fabric is then pulled off the needles by the take down rollers at a constant rate of speed. The mesh fabric is then taken up and wound onto a roll. The P4HB monofilament mesh produced according to this method may be scored ultrasonically with water, optionally heat set in hot water, and optionally washed with a 70% aqueous ethanol solution.

Absorbable expandable meshes may be prepared using the methods described herein, and used to produce implants that can be expanded by a tissue expander by 31 to 100%, preferably 35 to 75%, and even more preferably 45 to 65%. In one embodiment, the meshes comprise P4HB.

B. Implants with Sacrificial and Non-Sacrificial Fibers

In one embodiment, an absorbable expandable mesh may be prepared from the fibers described herein using a combination of sacrificial and non-sacrificial polymeric fibers. Sacrificial polymeric fiber as generally used herein means a fiber that is present initially in the implant, but degrades, yields, or breaks in vivo prior to the degradation, yielding, or breakage of a non-sacrificial component of the implant, such as a non-sacrificial polymeric fiber or strut. A sacrificial polymeric fiber or strut can initially enhance the strength or stability of the implant, but then is degraded or broken in order to allow the implant to expand in vivo, or is designed to yield under tension from the TE. Examples of sacrificial polymer fibers include: fibers that have low initial strength and can be broken, or that will yield, upon inflation of a tissue expander; fibers with small diameters that degrade faster than other components of the implant, such as fibers in the implant with larger diameters; fibers that degrade faster in the implant because they are not fully oriented; and fibers that degrade faster in the implant because they have a low weight average molecular weight. In one preferred embodiment, the absorbable expandable implants comprise sacrificial fibers comprising P4HB and copolymers thereof.

In an even more preferred embodiment, the absorbable expandable implants comprise both sacrificial and non-sacrificial fibers comprising P4HB and copolymers thereof. Sacrificial polymeric fibers made from P4HB and copolymers thereof may have one or more of the following properties: an elongation to break of 100-1,000%, tensile strength of 50-300 MPa, tensile modulus of 70-400 MPa, weight average molecular weight of 50-200 kPa, 50% in vivo strength retention or less after implantation for 1-12 weeks, and an average diameter of 10-500 microns. Non-sacrificial polymeric fibers made from P4HB and copolymers thereof may have one or more of the following properties: an elongation to break of 10-100%, tensile strength of 301-1,300 MPa, tensile modulus of 401-1,000 MPa, weight average molecular weight of 201-1,000 kPa, 50% in vivo strength retention after 13-104 weeks, and an average diameter of 10 microns to 1 mm. When compared to the non-sacrificial polymeric fibers, the sacrificial polymer fibers preferably have one or more of the following properties: smaller diameters, lower weight average molecular weights, lower tensile strength, shorter strength retention in vivo, and lower orientation of the polymer.

Figure 6:
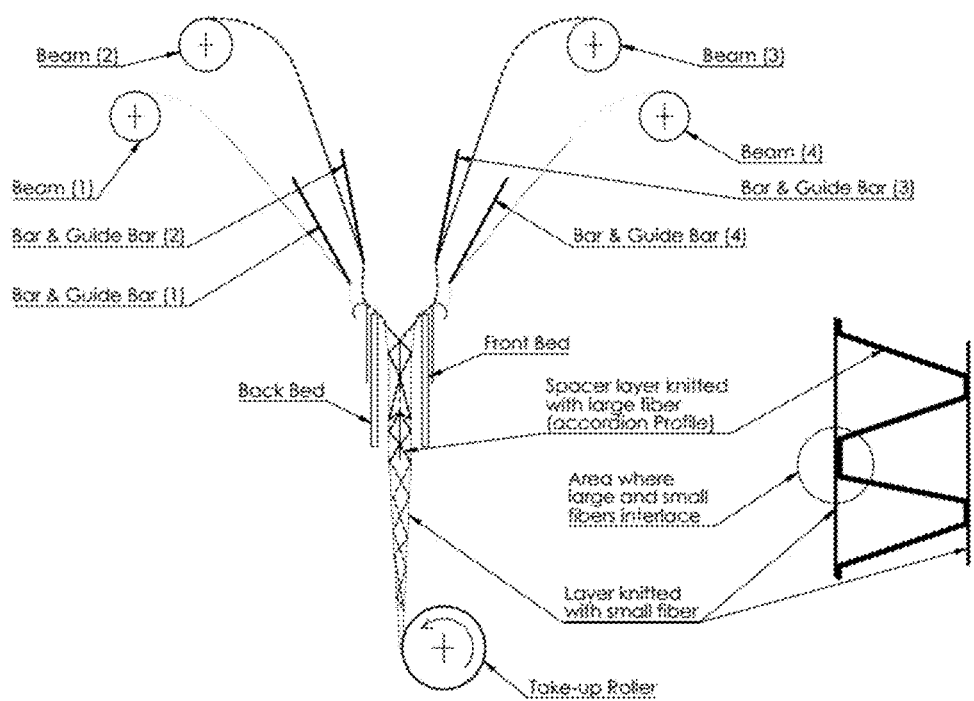
FIG. 6 is a diagram showing the equipment set up to produce an expandable absorbable implant made from a spacer fabric with small and large diameter monofilament fibers.
Figure 7:
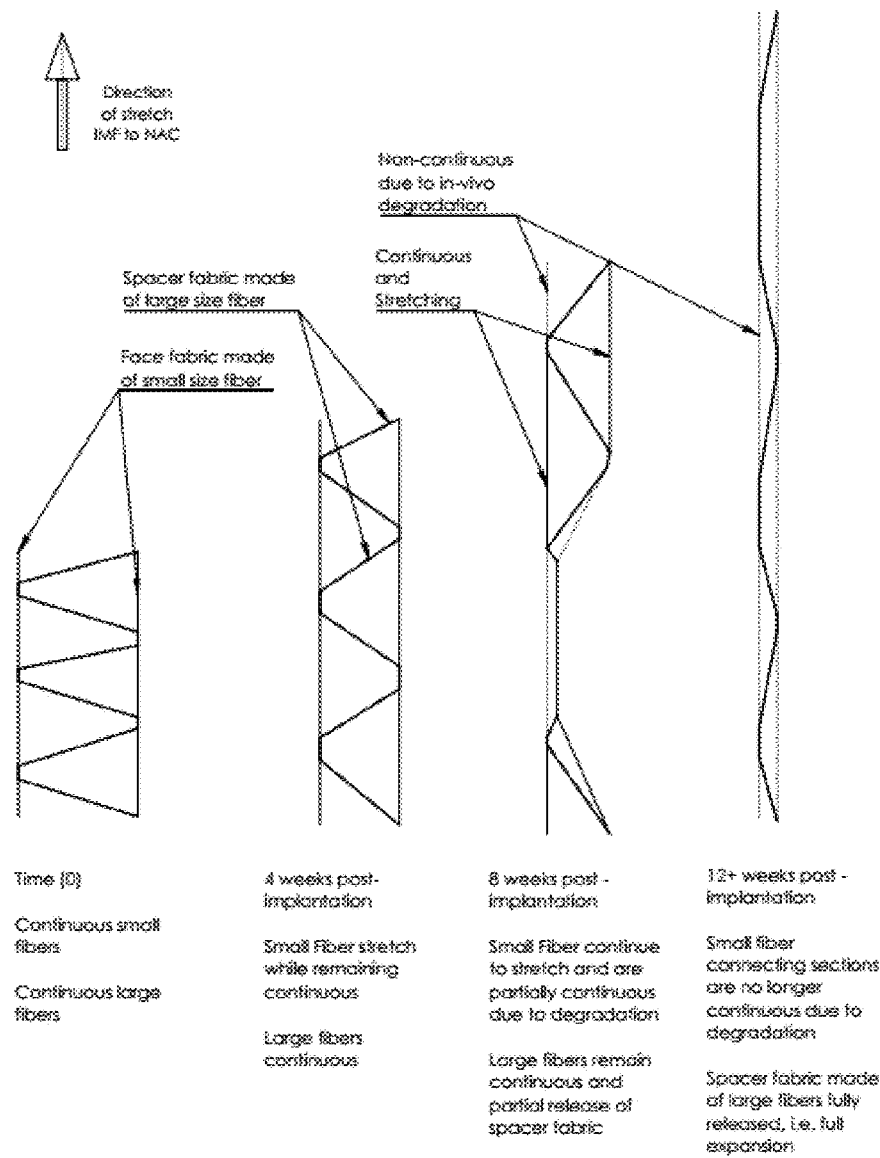
FIG. 7 is a diagram showing how the expandable absorbable implant prepared according to Example 6 can expand over a period of 4, 8 and 12 or more weeks after implantation.

Absorbable expandable meshes comprising sacrificial and non-sacrificial fibers of P4HB or copolymers thereof may be knit, for example, as described above using spools of sacrificial and non-sacrificial fibers of P4HB and copolymers thereof. FIG. 6 shows an alternative equipment set up for producing an expandable absorbable implant comprising sacrificial and non-sacrificial fibers, preferably comprising P4HB or copolymer thereof. This equipment set up can be used to produce a spacer fabric with sacrificial and non-sacrificial fibers, preferably comprising P4HB or copolymer thereof. FIG. 7 is a diagram showing how in one embodiment an expandable absorbable implant prepared according to Example 6 can expand over a period of 4, 8 and 12 or more weeks after implantation. The diagram shows how sacrificial fibers in the absorbable expandable mesh allow the implant to expand upon inflation of a tissue expander. These sacrificial fibers initially elongate to allow expansion of the implant, but also degrade faster than the non-sacrificial fibers. Over time, the sacrificial fibers degrade, may break, and permit further expansion of the absorbable expandable implant by the tissue expander. The spacer fabric may be produced using any combination of sacrificial fibers and non-sacrificial fibers. The sacrificial fibers preferably have one or more of the following: (i) low initial strength and can be broken upon inflation of a tissue expander before non-sacrificial fibers in the implant are broken; (ii) small diameters that degrade faster than other non-sacrificial components of the implant, such as fibers in the implant with larger diameters; (iii) faster degradation rates in the implant because they are not fully oriented when compared to non-sacrificial components of the implant; (iv) faster degradation rates in the implant because they are made from polymers with low weight average molecular weights; and (v) an ability to yield or stretch sooner and more than the non-sacrificial components in the implant. In a preferred embodiment, the sacrificial fibers with properties (i)-(v) comprise P4HB or copolymer thereof.

An example of the manufacture an expandable absorbable implant made with an oriented P4HB mesh and an inlaid sacrificial unoriented P4HB fiber is described in Example 4. An example of the manufacture of an expandable absorbable implant made with a sacrificial small diameter P4HB fiber is described in Example 5.

The exact time point and the tension at which the absorbable expandable implant made from sacrificial and non-sacrificial fibers can start to stretch may be controlled by selection of: the density of the fibers per unit area of the implant, the ratio of sacrificial to non-sacrificial fibers, the cross-sectional area of the fibers, the molecular orientation of the fibers, and the molecular weights of the fibers.

C. Implants with Sacrificial Struts

Figure 8:
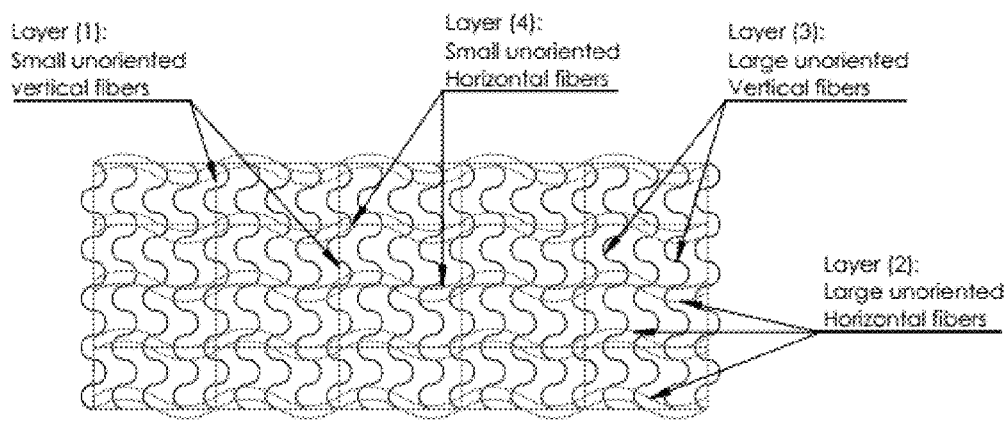
FIG. 8 is a diagram showing an expandable absorbable implant for breast reconstruction comprising a layer of small diameter low molecular weight vertical straight fibers, a second layer of large diameter high molecular weight horizontal wavy fibers, a third layer of large diameter high molecular weight vertical wavy fibers, and a fourth layer of small diameter low molecular weight horizontal straight fibers.
Figure 9:
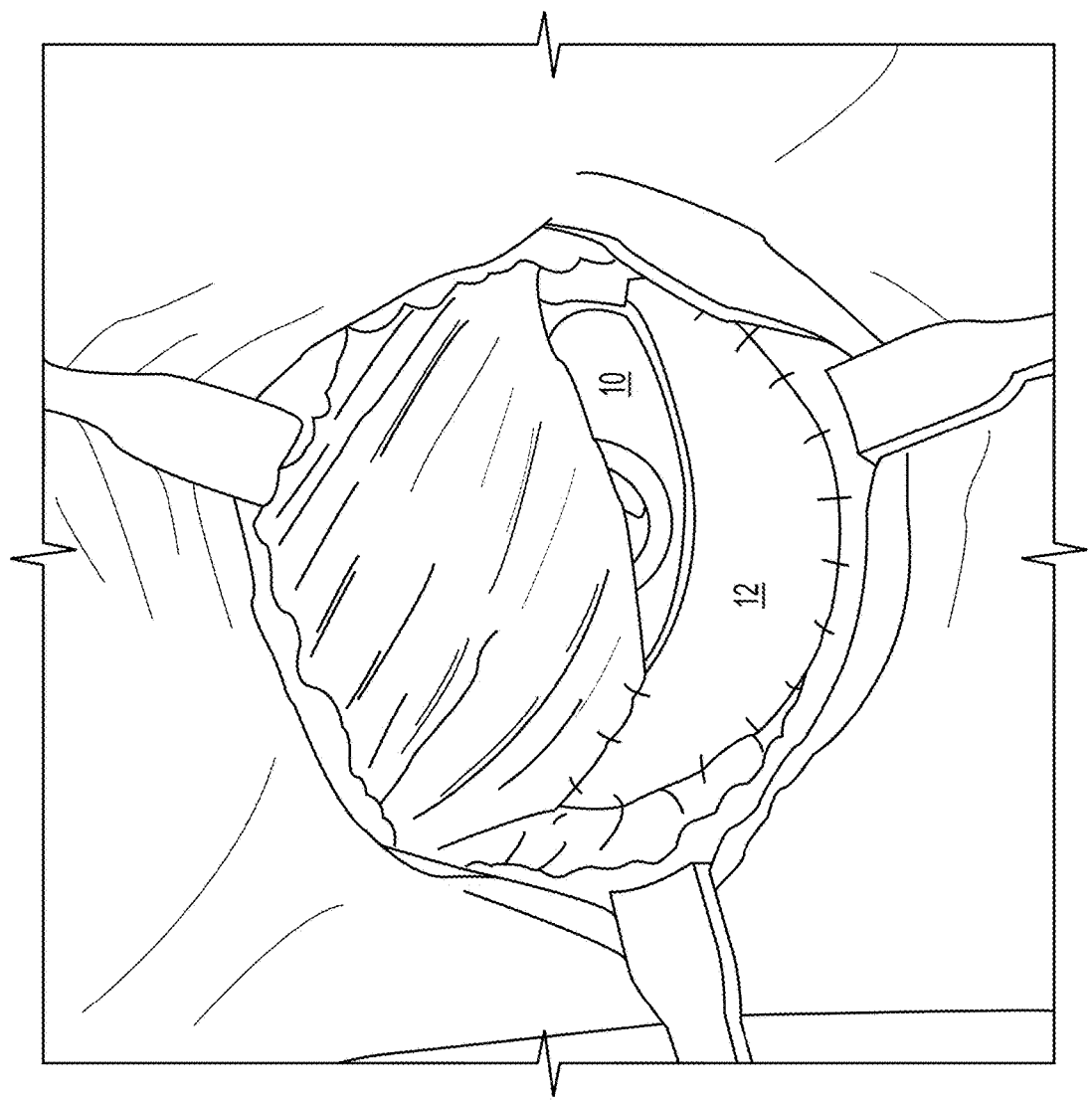
FIG. 9 is a schematic showing a tissue expander (10) positioned with the inferolateral portion of the tissue expander covered by an expandable breast implant (12).

The expandable absorbable implants may comprise struts, preferably polymeric struts, and even more preferably absorbable polymeric struts. The struts may be produced from the materials described in Section II A. The polymeric struts may be unoriented, partially oriented or fully oriented, but are preferably unoriented or partially oriented. The struts are preferably used in combination with another component, for example, fibers or meshes, to form the expandable absorbable implants. The struts may be rods or bars or other constructs that function to allow expansion of the implants while helping to provide appropriate structural architecture and initial strength. The struts are generally designed to be sacrificial in nature relative to other components of the implant that have a longer strength retention and do not stretch or break as easily. However, in certain embodiments the struts can be non-sacrificial in nature, or both sacrificial and non-sacrificial as shown in FIG. 8.

In vivo, the struts degrade and can be stretched or broken in order to allow the implant to expand. The struts may have a diameter or width. The struts may be arranged, for example, in parallel within the implant, or in any other suitable pattern to allow expansion of the implant at a given time. The struts may be arranged, for example, as a lattice or grid. The lattice or grid may comprise shaped spaces between the struts. For example, the shaped spaces between the struts can be square or diamond-shaped. A particularly preferred polymer for forming the struts is P4HB, or copolymer thereof. The sacrificial struts made from P4HB or copolymer thereof are preferably unoriented or partially oriented.

The absorbable expandable implants comprising polymeric struts should be capable of expanding in one or more dimensions by 31-100%, more preferably 35-75%, and even more preferably 45-65%. More preferably, the absorbable expandable implant comprising unoriented or partially oriented struts should be capable of expanding in one or more dimensions by 31-100%, more preferably 35-75%, and even more preferably 45-65%, within 6 months of implantation, and preferably from 10 days post-implantation to 8 weeks post-implantation.

The sacrificial struts may be manufactured by any suitable means, including extrusion, molding, pultrusion, spinning, including solution and melt spinning, and 3D printing. In a particularly preferred embodiment, the struts are formed from unoriented P4HB extrudate, for example, by extrusion or 3D printing.

D. Implants with Non-Sacrificial Mesh and Sacrificial Struts

In one embodiment, the absorbable expandable implant is formed from an absorbable non-sacrificial mesh and sacrificial struts. The absorbable mesh may comprise one or more of the following: unoriented fibers, partially oriented fibers or fully oriented fibers. The absorbable mesh may be produced, for example, by knitting, weaving, or crocheting. A particularly preferred mesh for use in preparing these expandable implants is a warp knit mesh. The absorbable mesh may have any suitable knit pattern, for example, the construction may be a Diamond, Diamond Plus, Crotchet, Delaware, Marquisette, Marquisette Plus or Marlex construction. A preferred knit pattern is a diamond knit pattern. The absorbable mesh may be produced from the materials disclosed herein. A particularly preferred absorbable mesh is made from fibers comprising P4HB or copolymers thereof, and even more preferably monofilament fibers comprising P4HB or copolymers thereof. One preferred method of producing an absorbable expandable implant comprising a P4HB mesh and sacrificial P4HB struts is to print the struts directly onto a P4HB mesh comprising oriented fibers using 3D printing. 3D Printing allows precise placement of the struts on the mesh, and allows the printed P4HB to fuse to the mesh without compromising the properties of the mesh. P4HB extrudate may be adhered to a P4HB mesh using, for example, a fusion deposition modeling (FDM) 3D-printer to deposit unoriented P4HB in a desired pattern by transforming the pattern into an STL file, and rendering into a two-slice 3D printing profile (Matter Control). This method of producing unoriented P4HB is particularly useful when production of composite implants, such as partially or fully oriented meshes comprising unoriented P4HB is required. In a typical procedure, P4HB extrudate can be deposited with an average diameter of 50 microns to 5 mm. In order to allow fusion of the P4HB extrudate to the P4HB mesh without damaging the underlying mesh, it is important that there is sufficient clearance between the print head and the mesh. In a particularly preferred embodiment, the P4HB extruding from the print head nozzle is cooled immediately to a temperature 56 to 63° C.

Figure 3:
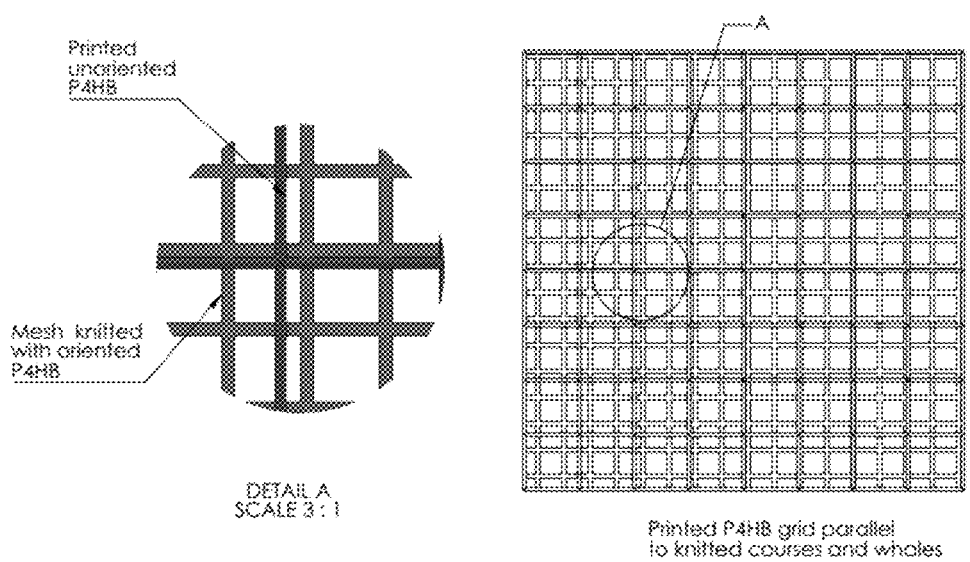
FIG. 3 is a diagram showing an expandable absorbable implant comprising an unoriented square lattice of P4HB struts that has been deposited over a knitted mesh wherein the unoriented lattice has been deposited along the loop edges of the knitted mesh.
Figure 5:
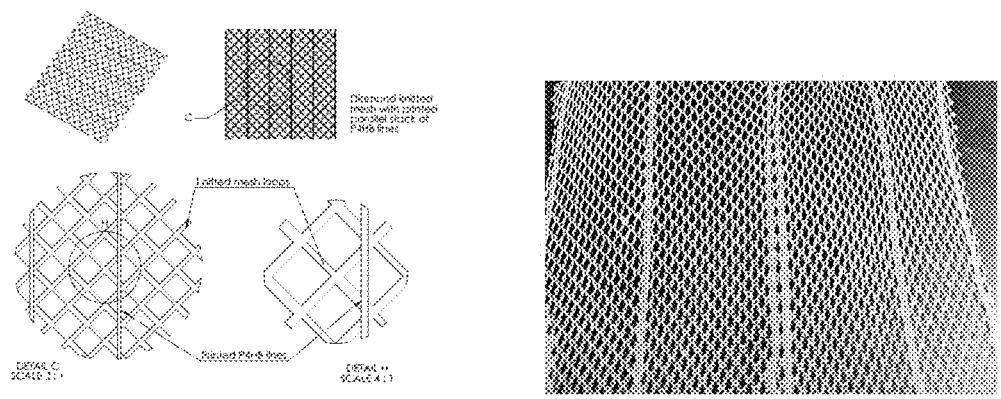
FIG. 5 is a picture of an expandable absorbable implant for breast reconstruction made from printing a series of parallel lines of unoriented P4HB struts on a diamond knitted P4HB mesh.

Example 1 describes the 3D printing of P4HB on an oriented P4HB non-sacrificial mesh with a diamond knit pattern to form an absorbable expandable implant that comprises the oriented P4HB mesh with a lattice or grid of sacrificial unoriented P4HB struts adhered to the mesh. In Example 1, the printed P4HB struts are positioned so that the deposited P4HB lattice was placed at a 45° angle to the mesh loops as shown in FIG. 1. In alternative embodiments, meshes, preferably partially or fully oriented meshes comprising P4HB or copolymer thereof, can be prepared with different knit patterns, and absorbable expandable implants formed by 3D printing sacrificial struts of P4HB or copolymers thereof either at a 45° angle to the mesh loops, or in any other angle (1° to 90° angles) or pattern on the mesh. The struts may be printed on the meshes to form lattices or grids, or may be printed in parallel to one another on the meshes. For example, FIG. 3 shows how an absorbable expandable implant can be formed by 3D printing sacrificial P4HB struts on a P4HB oriented mesh so that the struts run parallel to the knit courses and whales. And FIG. 5 shows an example of an implant made from a P4HB oriented mesh with a parallel series of sacrificial P4HB struts printed on the mesh at a 45° angle to the mesh loops. The preparation of the implant shown in FIG. 5 is described in Example 3.

In another embodiment, the absorbable expandable implants can be formed by fusing preformed sacrificial polymeric struts to a non-sacrificial mesh. Preferably, the sacrificial polymeric struts are unoriented or partially oriented, and the mesh comprises fibers that are partially or fully oriented. In a preferred embodiment, the polymeric struts are made from P4HB or copolymer thereof, and either unoriented or partially oriented. In a particularly preferred embodiment, the polymeric struts are unoriented melt extrudate of P4HB or copolymer thereof. In another preferred embodiment, the mesh is made from partially or fully oriented fibers of P4HB or copolymer thereof, and the implant is produced by fusing sacrificial unoriented melt extrudate of P4HB or copolymer thereof to the mesh to form struts on the mesh. Example 2 describes how an absorbable expandable implant can be formed by fusing sacrificial unoriented P4HB struts to a non-sacrificial P4HB mesh comprising oriented P4HB fibers with a diamond knit pattern. FIG. 4(*a*) is a picture showing sacrificial P4HB struts laid on an oriented P4HB mesh (positioned over a silicone pad) prior to fusing the struts to the mesh. The struts are placed on the mesh so that they form a grid, and the grid in this example is placed at a 45° angle to the mesh loops. The struts are then fused to the mesh by inserting the assembly into a flat mold, applying pressure to the assembly, and placing the mold containing the assembly in a hot water bath at a temperature of 57° C. for 5 minutes to fuse the unoriented P4HB sacrificial extrudate to the non-sacrificial mesh. The expandable absorbable implant formed by this method is shown in FIG. 4(*b*). It should be noted that the silicone pad allows uniform tension to be applied to the mesh, and prevents undesirable shrinkage of the mesh during fusion. Variations of this procedure may be used to fuse struts to meshes in different patterns, at different angles (e.g. from 0° to 90°) to the knit pattern and in different arrangements.

The exact time point and the tension at which the absorbable expandable implant made from non-sacrificial mesh and sacrificial struts can start to stretch may be controlled by selection of: the density of the fibers per unit area of the mesh, the density of sacrificial struts, the pattern of the struts on the mesh, the ratio of mesh fibers to sacrificial struts, the molecular orientation of the mesh fibers and struts, the cross-sectional area of the fibers and struts, and the molecular weights of the fibers.

E. Implants with Large Cross-Sectional Struts or Fibers and Smaller Cross-Sectional Sacrificial Struts or Fiber In a further embodiment, the absorbable expandable implants may comprise unoriented struts or fibers of different geometries, sizes (i.e. cross-sections), and molecular weights or combinations thereof. Unoriented P4HB absorbable fibers or struts with large cross-sections (e.g. diameters or widths of 200-400 microns) and weight average molecular weights of 300-500 kDa can maintain their integrity in vivo beyond 6 months, and serve as non-sacrificial components of an absorbable expandable implant. These fibers or struts can be extruded or printed with an inherent capacity to expand, for example, ranging from 20% to 100% depending upon the geometry selected. Their immediate ability to expand in an implant, however, can be temporarily prevented by incorporating a network of smaller sacrificial cross-sectional unoriented fibers or struts into the implant. These smaller sacrificial fibers or struts can be made, for example, from unoriented P4HB fiber or struts with a weight average molecular weight of 50-300 kDa, more preferably 50-200 kDa, and a cross-sectional diameter or dimension (e.g. width) of 80-200 microns such that the implant is able to stretch (i.e. expand) within 1-12 weeks of implantation, more preferably 2-8 weeks of implantation, and even more preferably 2-6 weeks of implantation. The exact time point and the tension at which the absorbable expandable implants made from the large cross-sectional struts or fibers and smaller cross-sectional sacrificial struts or fiber can start to stretch is controlled by the density of the fibers or struts per unit area of the implant, the molecular weights of the struts or fibers, the molecular orientation of the struts or fibers, and the cross-sectional area of the larger unoriented fibers or struts.

F. Implants Using Fiber Geometry to Control Expansion

The implants may incorporate components, such as fibers and struts, with geometries that can control the expansion of the implants. In one embodiment, the implants may comprise components that are not initially under tension at the time of implant, but become under tension post-implantation. These components may reduce or limit further expansion of the implant at least until the component degrades to the point where it does not resist stretching by the TE. For example, the implants may comprise components that zig-zag through the implant, and become straight and under tension from the TE as the implant is expanded. Alternatively, the implants may comprise wavy or curly components that become straight and are placed under tension post-implantation as the TE is inflated, or the implants may comprise components formed into loops wherein the diameters of the loops decrease and eventually the components become linear as the implants are expanded and the components placed under tension. These different component geometries (e.g. zig-zag, wavy and loops) may be constructed, using for example fibers and 3D printing, and the constructs may be made with oriented, partially oriented or fully oriented polymeric materials that have Mw ranging from 50 kDa to 600 KDa.

The preparation of an absorbable expandable implant comprising non-sacrificial large diameter wavy struts is described in Example 8. The implant comprises sacrificial small diameter, low Mw, unoriented P4HB struts in the form of a grid and larger diameter non-sacrificial P4HB struts organized in a wavy pattern that allow expansion of the implant as the smaller diameter sacrificial struts degrade.

Examples 9 and 10 illustrate other methods for forming absorbable expandable implants using components with different geometries. Example 9 describes the preparation of an implant using a printed grid of unoriented small diameter absorbable struts with short strength retention incorporating a wavy fiber with prolonged strength retention. Example 10 describes an implant prepared from a spunlaid fabric with short strength retention incorporating a wavy fiber with prolonged strength retention.

G. Implants Comprising Stretchable Components

In another embodiment, an absorbable expandable implant may be prepared from unoriented or partially oriented fibers, or a combination thereof, formed into a mesh. Such meshes are designed so that they have the ability to stretch when inflated by a tissue expander in order to form a submuscular pocket for a breast implant. In this embodiment, it is important that the mesh can be expanded by the force applied by the tissue expander. Typical forces applied by tissue expanders range between 0.2 and 22 N/cm, more preferably between 0.6 and 12 N/cm and even more preferably between 1 and 9 N/cm. The absorbable expandable mesh made from unoriented or partially oriented fibers should be capable of expanding in one or more dimensions by 31-100%, more preferably 35-75%, and even more preferably 45-65%. More preferably, the absorbable expandable mesh made from unoriented or partially oriented fibers should be capable of expanding in one or more dimensions by 31-100%, more preferably 35-75%, and even more preferably 45-65%, within 6 months of implantation, and preferably from 10 days post-implantation to 8 weeks post-implantation.

The absorbable expandable mesh implants with unoriented or partially oriented fibers may be prepared with the fibers disclosed herein. In a particularly preferred embodiment, these implants are made with unoriented or partially oriented P4HB fibers, or combinations thereof. More preferably, these fibers are monofilament fibers. Spools of unoriented or partially oriented P4HB monofilament fiber, or combinations thereof may be converted into an expandable absorbable implant for breast reconstruction as follows: The unoriented or partially oriented P4HB fiber on 49 spools is mounted on a creel, aligned side by side and pulled under uniform tension to the upper surface of a "kiss" roller. The "kiss" roller is spun while semi-immersed in a bath filled with a 10% solution of Tween® 20 lubricant. The Tween® 20 lubricant is deposited on the surface of the sheet of fiber. Following the application of Tween® 20, the sheet of fiber is passed into a comb guide and then wound on a warp beam. A warp is a large wide cylinder onto which individual fibers are wound in parallel to provide a sheet of fibers. Next, warp beams are converted into a finished mesh by means of interlocking knit loops. Eight warp beams are mounted in parallel onto tricot machine let-offs and fed into the knitting elements at a constant rate determined by the 'runner length'. Each individual monofilament fiber from each beam is fed through a series of dynamic tension elements down into the knitting 'guides'. Each fiber is passed through a single guide, which is fixed to a guide bar. The guide bar directs the fibers around the needles forming the mesh structure. The mesh is then pulled off the needles by the take down rollers at a constant rate of speed determined by the fabric 'quality'. The mesh with unoriented or partially oriented P4HB fibers, or combinations thereof is then taken up and wound onto a roll and scored ultrasonically with water, and then washed with a 70% aqueous ethanol solution. The unoriented or partially oriented mesh, so obtained, having not been oriented to the maximum amount possible, allows for delayed expansion of the mesh in the breast by further stretching using a tissue expander.

The exact time point and the tension at which the absorbable expandable implants made from stretchable components, such as unoriented or partially oriented fibers, can start to stretch is controlled by the density of the fibers in the implant, the cross-sectional area of the fibers, the molecular orientation of the fibers, and the molecular weight of the fibers.

An example of an implant made from a stretchable component is described in Example 7.

H. Properties and Dimensions of the Implants

The absorbable expandable implants preferably have a thickness between 0.5-5 mm, more preferably between 1-4 mm, and even more preferably between 2-3 mm. These thicknesses are particularly advantageous in breast reconstruction for helping to generate a pocket for a breast implant. A thickness of 2-5 mm, more preferably 2-3 mm is particularly preferred for providing a better aesthetic outcome. Implants with thicknesses greater than 2 mm can be used, for example, to mask wrinkles that otherwise may be visible on the surface of the body.

The implants of the invention described herein may further comprise other materials. In particular, the implants may comprise other materials for the purpose of increasing the thickness of the implant. For example, the implants described herein may be further combined with porous materials such as fibrous constructs, including spunlaid, spunbond, non-wovens, melt-blown, dry spun, electrospun, porous thermoforms and laminates, and perforated films and sheets.

The expandable absorbable implants preferably have one or more of the following properties: a suture pullout strength between 10 gf, and 20 kgf, and more preferably 100 gf and 5 kgf; an endotoxin content of less than 20 endotoxin units; an ability for the implant to be expanded in vivo by a tissue expander by 31% to 100%, preferably by 35% to 75%, and more preferably by 45% to 65%; an ability to be expanded by a tissue expander within 4 months of implantation, preferably within 3 months of implantation, and more preferably within 2 months of implantation, and even more preferably within 10 days of implantation; dimensions from 5 cm×15 cm to 15 cm×30 cm, and thickness of 0.5-5 mm; average pore diameter between 75 microns and 5 mm; fibers or struts with a diameter or width between 10 microns and 1 mm; sacrificial polymeric fibers or struts that have an elongation at break of between 100% and 1,000%, tensile strength between 50 MPa and 300 MPa, tensile modulus between 70 MPa and 400 MPa, fibers or struts with an average diameter or width of 10 microns to 500 microns; non-sacrificial polymeric fibers or struts that have an elongation to break between 10% and 100%, tensile strength between 301 and 1,300 MPa, tensile modulus between 401 and 1 GPa, fibers or struts with an average diameter or width of 10 microns to 1 mm; strength retention in vivo of at least 40% of its original tensile strength or burst strength; a time to complete absorption in the body of 2 years or less; an ability to be expanded by a tissue expander in vivo when the tissue expander is inflated with 1 cc to 150 cc of fluid or gas on one or more occasions, and an ability to be expanded by a tissue expander in vivo when the force applied by the expanding tissue expander is between 0.2 and 22 N/cm, more preferably between 0.6 and 12 N/cm and even more preferably between 1 and 9 N/cm.

The absorbable expandable implants may further comprise the bioactive agents described in Section II.C.

I. Implant Constructions

A description of the components of some of the absorbable expandable implants contemplated herein that are made with sacrificial and non-sacrificial components is given in Table 1 for illustration purposes. In a preferred embodiment, the components shown in Table 1 comprise P4HB or copolymer thereof. In general, the sacrificial components comprising P4HB or copolymer thereof have short strength retention, and the non-sacrificial components have prolonged strength retention. Short strength retention means that the component yields, breaks, or stretches when tension is applied by a TE in the period from the time of implant to 3 months post-implantation. Prolonged strength retention means that there is no stretching, or less than 20% stretching, of the component when tension is applied by a TE in the period from the time of implant to 3 months post-implantation. The sacrificial components incorporated into the implants and comprising P4HB or copolymer thereof have one or more of the following properties: (i) fast degradation, (ii) low weight average molecular weight, (iii) low tensile strength, (iv) low resistance to stretching, (v) smaller cross-sections, (vi) unoriented or partially oriented structure, and (vii) high elongation to break (100%-1,100%). These properties allow the sacrificial components to yield, break, or stretch upon inflation of the TE.

TABLE 1

| # | Non-sacrificial component | Sacrificial component | Implant construction |
|---|---|---|---|
| 1 | Oriented mesh | Unoriented struts | Struts 3D printed on mesh |
| 2 | Oriented mesh | Grid of unoriented struts | Struts fused to mesh |
| 3 | Oriented mesh | Parallel lines of struts | Struts fused to mesh |
| 4 | Large diameter fiber | Small diameter fiber | Knit or woven fabric, including spacer fabric |
| 5 | Wavy large diameter unoriented fiber | Grid of small diameter unoriented fiber | Wavy fiber sewn into grid |
| 6 | Oriented mesh | Unoriented and partially oriented fiber | Unoriented or partially oriented fiber inlaid in oriented mesh |
| 7 | Oriented mesh | Oriented fiber with smaller diameters than mesh fibers | Unoriented fiber inlaid in oriented mesh |
| 8 | Wavy oriented fiber | Lattice with small diameter unoriented struts | Wavy fiber inserted or sewn in lattice |
| 9 | Wavy unoriented fiber | Lattice of small diameter unoriented struts | Wavy fiber inserted or sewn in lattice |
| 10 | Wavy oriented fiber | Spunlaid or spunbond | Wavy fiber inserted or sewn in spunlaid or spunbond |

IV. Methods of Implanting and Expanding

The implants may be implanted in the body. Preferably, the implants are used in tissue regeneration and repair, and in particular as slings or hammocks, and particularly for generating pockets. In a particularly preferred embodiment, the implants are used in breast reconstruction procedures, especially following mastectomy, and can be used with a tissue expander to create a pocket for a breast implant. In a typical breast reconstruction procedure, the method of implantation comprises (i) implanting a tissue expander in the patient; (ii) implanting the absorbable expandable implant in the vicinity of the tissue expander; (iii) expanding the tissue expander; (iv) removing the tissue expander; and (v) implanting a breast implant in the patient. In a particularly preferred embodiment, the method involves the use of the implant as a pectoralis extender to create the submuscular pocket for a permanent breast implant. The implants are preferably sutured to the detached pectoralis major muscle, which has been mobilized in preparation for placement of a tissue expander. The suture may be either permanent or absorbable, but is preferably absorbable. Once sutured to the pectoralis major muscle, the implants can be used as a sling or hammock to cover the inferolateral portion of an inserted tissue expander. The tissue expander may be partially inflated or uninflated prior to implantation. In the latter case, the tissue expander may be partially inflated immediately after implantation.

The protocol for expansion of the tissue expander will be determined by the individual circumstances, and the type of tissue expander used. Expansion may begin immediately after implantation or may be delayed for several days or weeks. In one embodiment, tissue expansion is started immediately after implantation. This is more typical when a gas is used for inflation of the tissue expander. In a preferred embodiment, tissue expansion is started 10 to 14 days after implantation of the tissue expander. This is more typical when saline is used to inflate the tissue expander. The frequency of expansion will also depend upon the individual circumstances, and the type of tissue expander used. Expansion may be performed continuously, daily, or weekly. Gas-based tissue expanders may be inflated gradually, preferably daily, and can be programmed for remote expansion by the physician. When saline-based tissue expanders are implanted, the expander is typically inflated every 1-4 weeks, and in consultation with the patient. Saline-based tissue expanders are inflated by injection of saline into the expander. Typical volumes of saline used to inflate the expander are 60-120 cm$^3$. The actual volume administered will be dictated by patient tolerance and the clinical appearance. In general, a more rapid expansion is preferred in order to avoid excessive scar formation, and it is preferable to complete the expansion within 2 months. Due to relaxation of tissues after expansion is completed, it is often preferable to overexpand the tissue expander by 10-20% of the required or target volume. The timing of the exchange of the tissue expander for a permanent breast implant will vary depending upon individual patient circumstances. The exchange may be performed anytime after completion of expansion, but typically between 6 weeks and 6 months after the final expansion. Suitable breast implants include saline breast implants and silicon breast implants.

The implants may be produced in any suitable size for implantation. For breast reconstruction, the size will vary according to the size of the tissue expander, breast implant and pectoralis muscle. In a preferred embodiment, the implants have dimensions that are from 5 cm×15 cm to 15 cm×30 cm. A typical implant size is 8×16 cm. The implants may, if necessary, be cut or trimmed prior to implantation.

The present invention will be further understood by reference to the following non-limiting examples.

Example 1: Manufacture of Expandable Absorbable Implants for Breast Reconstruction Using a Diamond Non-Sacrificial Mesh Knitted with Oriented P4HB Monofilaments and a Printed Sacrificial Unoriented Grid of P4HB Struts An expandable absorbable implant for breast reconstruction was prepared as follows. A non-sacrificial P4HB mesh was knit with a diamond knit pattern using oriented P4HB monofilament (Mw 340 kDa) with an average diameter of 80 microns. The average density of the knitted P4HB mesh was 130 g/m². A fusion deposition modeling (FDM) 3D-printer was then used to deposit a square lattice of sacrificial unoriented P4HB struts over the non-sacrificial knitted mesh so that deposited sacrificial P4HB lattice was placed at a 45° angle to the mesh loops as shown in FIG. 1. The P4HB lattice pattern was transformed into an STL file, and rendered into a two-slice 3D printing profile (Matter Control) with a slice (layer) height of 0.25 mm. The average diameter of the deposited P4HB lattice was 2.9±0.1 mm, and the P4HB had a Mw of 230 kDa. A P4HB feed rate of 0.22 mm/s was used, and the P4HB was passed through a flexible hot end with an extruder nozzle size of 0.6 mm. The extruder temperature was set to 280° C., and the print speed kept at 6.5 mm/s. The printing stage was set to 25° C. The temperature at the transition zone was kept at 36 to 38° C. using a custom compressed air feed and dispersion plate, and the filament temperature at the linear mechanical feeder was 28 to 30° C. To allow fusion of the sacrificial extrudate to the underlying mesh and prevent searing of the mesh, the print head was offset to allow for 0.3 mm of clearance from the mesh, and a dual air blower was added to immediately cool the P4HB strut extruding from the nozzle to a temperature of 56 to 63° C. The density of the unoriented P4HB lattice averaged 17.8 g/m².

A second expandable absorbable implant for breast reconstruction was prepared using the method above, except the sacrificial P4HB lattice was deposited on the non-sacrificial mesh with the diamond knit pattern so that the polymer was deposited along the loop edges of the knitted mesh as shown in FIG. 3. The spacing and amount of the printed unoriented P4HB struts deposited on the mesh were adjusted so that the density of the unoriented P4HB struts on the final implant averaged 17.8 g/m².

Example 2: Manufacture of Expandable Absorbable Implants for Breast Reconstruction Using a Non-Sacrificial Diamond Mesh Knitted with Oriented P4HB Monofilaments Fused to a Sacrificial Grid of Unoriented P4HB Extrudate An expandable absorbable implant was prepared using the non-sacrificial diamond knitted P4HB mesh described in Example 1, but the mesh was heat fused with a sacrificial grid prepared from unoriented P4HB extrudate. The grid was prepared using 0.6 mm diameter P4HB extrudate (Mw 230 kDa) that had been cut into 15 cm length strands, and placed in a square grid conformation on top of a 10 cm×10 cm diamond mesh lying on a ⅟16″ thick silicone pad as shown in FIG. 4(a). The grid of P4HB extrudate was placed at a 45° angle to the mesh loops. The assembly was then inserted into a flat mold, tightened to apply pressure, and placed in a hot water bath at a temperature of 57° C. for 5 minutes to fuse the unoriented P4HB extrudate to the diamond mesh. The resulting product is shown in FIG. 4(b). The silicone pad was added to provide uniform tension to the mesh, and prevent undesired mesh shrinkage.

Example 3: Manufacture of Expandable Absorbable Implants for Breast Reconstruction Using a Non-Sacrificial Diamond Mesh Knitted with Oriented P4HB Monofilaments Fused to a Parallel Stack of Sacrificial Unoriented P4HB Extrudate An expandable absorbable implant was prepared as described in Example 2, but instead of fusing the mesh to a grid of unoriented P4HB extrudate, the non-sacrificial mesh was fused to a series of parallel lines of sacrificial unoriented P4HB extrudate with a diameter of 0.6 mm as shown in FIG. 5.

Example 4: Manufacture of Expandable Absorbable Implants for Breast Reconstruction Comprising Diamond Mesh Knitted with Non-Sacrificial Oriented P4HB Monofilaments and an Inlaid Unoriented P4HB Extrudate Sacrificial Fiber An expandable absorbable implant was prepared with the design shown in FIG. 1, but instead of depositing the unoriented P4HB on the mesh, an unoriented P4HB sacrificial extrudate fiber of 0.6 mm diameter was knit with P4HB non-sacrificial oriented monofilament fiber (80-100 µm diameter) so that the unoriented P4HB extrudate was present as a sacrificial inlay fiber in the knitted mesh. This was accomplished by loading the unoriented extrudate into the knitting machine along with oriented P4HB monofilament fibers, and inserting the unoriented extrudate using a dedicated inlay bar of the warp knitting machine so that the unoriented extrudate did not form loops (i.e. is not caught by the needle head), and instead was trapped between the loops of the P4HB oriented monofilament fibers being knit on two separate and dedicated bars. A stitch density of 20 stitches per cm was used to prepare the diamond mesh.

Example 5: Manufacture of Expandable Absorbable Implants for Breast Reconstruction Comprising a Diamond Mesh Knitted with Non-Sacrificial Oriented P4HB Monofilaments and an Inlaid Sacrificial Oriented P4HB Fiber of Smaller Diameter An expandable absorbable implant for breast reconstruction may be prepared as described in Example 4, but instead of inlaying an unoriented P4HB monofilament fiber with a diameter of 0.6 mm into the mesh, a sacrificial P4HB monofilament fiber with an average diameter of only 40 microns may be knit with the non-sacrificial P4HB oriented monofilament (80-100 μm diameter) as an inlay sacrificial fiber.

Example 6: Manufacture of Expandable Absorbable Implants for Breast Reconstruction Comprising a Mesh Made with a Spacer Fabric Design Using Large Diameter Oriented P4HB Non-Sacrificial Monofilament Fibers and Sacrificial Smaller Diameter Oriented P4HB Monofilament Fibers An expandable absorbable implant for breast reconstruction with a spacer fabric design may be prepared using a double needle bed warp knitting machine. The setup of the machine that can be used is shown in FIG. 6, and includes a 14-gauge needle bed, 4 guide bars, and 4 yarn beams. The implant can be constructed using two beams wound with a small diameter size sacrificial oriented P4HB monofilament fiber (average diameter of 40 microns) with a Mw of 200-250 kDa, and the other two beams wound with a larger diameter size non-sacrificial oriented P4HB monofilament fiber (average diameter of 100-150 microns) with a higher Mw of 300-400 kDa. With reference to FIG. 6, the smaller diameter fibers are threaded through the outer beams (1 and 4) while the larger diameter fibers are threaded through the center beams (2 and 3). The fiber on the center beams (2 and 3) is used to knit the accordion like structure zigzagging between the front and back bed while the fiber on the outer beams (1 and 4) is used to knit a loose open stitch pattern on the back and front beds. The two outer layers made from the smaller sacrificial fibers are designed to degrade first after implantation allowing the mesh to be expanded in vivo as the trapped accordion structure is released.

Example 7: Manufacture of Expandable Absorbable Implants for Breast Reconstruction Comprising a Mesh Made from Partially Oriented P4HB Monofilament Fibers A partially oriented P4HB monofilament fiber was first prepared using the following method. Bulk P4HB resin in pellet form was dried to less than 300 ppm water content using a rotary vane vacuum pump system. The dried resin was transferred to an extruder feed hopper with nitrogen purge to keep the pellets dry. The pellets were gravity fed into a chilled feeder section and introduced into the extruder barrel, which was 1.50 inches in diameter and fitted with an extrusion screw with a 30:1 L/D ratio. The extruder barrel contained 5 heating zones (or extrusion zones)—zones 1, 2, 3, 4 and 5, and was manufactured by American Kuhne. The heated and homogenized melted resin from the extruder was fed into a heated metering pump (melt pump) and from the melt pump the extruded resin was fed into the heated block and an eight-hole spinneret assembly. Processing profile ranges from 40° C. to 260° C. for temperatures, and 400 psi to 2000 psi for pressures, were used. The molten filaments were water quenched (at a temperature of 5° C. to 30° C.), allowed time to crystallize, and then partially oriented at ambient temperature (14-30° C.) with an orientation ratio of 3.5-3.7. It should be noted that the filaments were intentionally partially oriented below an orientation ratio of 4.0 to provide enough strength to accommodate knitting tension during conversion of the filaments to mesh.

The spools of partially oriented P4HB fiber were converted into an expandable absorbable implant for breast reconstruction as follows: The partially oriented P4HB fiber on 49 spools was mounted on a creel, aligned side by side and pulled under uniform tension to the upper surface of a "kiss" roller. The "kiss" roller was spun while semi-immersed in a bath filled with a 10% solution of Tween® 20 lubricant. The Tween® 20 lubricant was deposited on the surface of the sheet of fiber. Following the application of Tween® 20, the sheet of fiber was passed into a comb guide and then wound on a warp beam. A warp is a large wide cylinder onto which individual fibers are wound in parallel to provide a sheet of fibers. Next, warp beams were converted into a finished mesh by means of interlocking knit loops. Eight warp beams were mounted in parallel onto tricot machine let-offs and fed into the knitting elements at a constant rate determined by the 'runner length'. Each individual monofilament fiber from each beam was fed through a series of dynamic tension elements down into the knitting 'guides'. Each fiber was passed through a single guide, which was fixed to a guide bar. The guide bar directed the fibers around the needles forming the mesh structure. The mesh was then pulled off the needles by the take down rollers at a constant rate of speed determined by the fabric 'quality'. The mesh with partially oriented P4HB fibers was then taken up and wound onto a roll and scoured ultrasonically with water, heat set at 54° C.±3° C. in hot water and then washed with a 70% aqueous ethanol solution. The partially oriented mesh implant, so obtained, having not been oriented to the maximum amount possible, allows for delayed expansion of the mesh in the breast by further stretching using a tissue expander.

Example 8: Manufacture of an Expandable Absorbable Implant Made with a Printed Wavy Pattern of Large Diameter Non-Sacrificial Unoriented P4HB Struts and a Printed Grid Pattern of Small Diameter Sacrificial Unoriented P4HB Struts In this example and as depicted in FIG. 8, high molecular weight P4HB non-sacrificial unoriented extrudate (Mw 380 kDa) was 3D printed using the FDM printer described in Example 1 to form a wavy base pattern with an average strut diameter of 350 microns. The wavy pattern consisted of high molecular weight non-sacrificial struts running in vertical and horizontal directions that were printed using a 0.35 mm nozzle size and the same print settings that were used in Example 1. The wavy pattern of high molecular weight struts was sandwiched between two layers of sacrificial smaller diameter low molecular weight P4HB struts (160 microns average diameter and Mw 120 kDa) that were also printed using the same print settings described in Example 1, except that the nozzle size used was 0.15 mm and the feed rate was 0.15 mm/sec. The smaller diameter sacrificial struts were printed in straight lines either vertically or horizontally. The order of printing for the whole implant was: Layer (1), small diameter low Mw vertical straight sacrificial struts; Layer (2), large diameter high Mw horizontal wavy struts; Layer (3), large diameter high Mw vertical wavy struts; and Layer (4), small diameter low Mw horizontal straight sacrificial struts. In this example, the wavy pattern consisted of a sinusoidal pattern with the wavelength ($\lambda$) and amplitude (A) of the sinusoidal wave set to allow expansion of the implant in vivo in the IMF (inframammary fold) to NAC (nipple-areolar-complex) direction by up to 60%, and in the medial to lateral direction by up to 10%. In the IMF to NAC direction, the amplitude and wavelength of the sinusoidal wave were set at 4.4 mm and 8 mm, respectively, and in the medial to lateral direction the amplitude and wavelength were set at 4.6 mm and 20 mm.

The dimensions for alternative expandable absorbable implants with different expansion targets (p) may be calculated from Equation (1):

$$A = \frac{\lambda}{2}\sqrt{(1+\rho)^2 - 1}$$

Example 9: Manufacture of an Absorbable Expandable Implant Made with a Printed Grid Pattern of Small Diameter Unoriented P4HB Sacrificial Struts with a Wavy Pattern of Oriented Non-Sacrificial P4HB Fiber An absorbable expandable implant was prepared according to the method of Example 8, except the wavy patterns (layers 2 and 3) were made from size 5-0 oriented non-sacrificial P4HB monofilament fiber (Mw 340 kDa) instead of unoriented large diameter non-sacrificial struts. The implant was prepared by sewing the oriented non-sacrificial P4HB monofilament fiber into a pre-printed lattice of small diameter unoriented sacrificial P4HB struts (Mw 120 kDa).

Example 10: Manufacture of an Absorbable Implant Made with an Unoriented P4HB Spunlaid Sacrificial Fabric with a Wavy Pattern of Oriented Non-Sacrificial P4HB Fiber An absorbable expandable implant was prepared according to the method of Example 8, except layers 1 and 4 were replaced by a loose web of sacrificial spunlaid unoriented P4HB fibers with an average thickness of 0.15 mm, and the wavy pattern (layers 2 and 3) was made from size 5-0 oriented non-sacrificial P4HB monofilament fiber (Mw 340 kDa) instead of unoriented fiber by sewing the monofilament fiber into the spunlaid.

In an alternate implant construction, the sacrificial P4HB spunlaid may be replaced by a sacrificial P4HB spunbonded web.

Modifications and variations of the methods and compositions will be apparent from the foregoing detailed description and are intended to come within the scope of the appended claims.

We claim:

1. An expandable absorbable breast implant comprising a spacer fabric, wherein the spacer fabric comprises a first outer face layer and a second outer face layer opposed to and spaced from the first outer face layer, the first and second opposed and spaced outer face layers formed of sacrificial polymeric fibers and connected by non-sacrificial polymeric fibers extending between the first and second opposed and spaced outer face layers.

2. The implant of claim 1, wherein one or more dimensions of the implant are expandable by 45% to 100% when placed in the vicinity of a tissue expander by attaching the implant to a pectoralis major muscle, by inflation of the tissue expander, within 4 months of implantation.

3. The implant of claim 1, wherein the implant has one or more of the following properties: (i) a thickness between 100 μm and 1 cm; (ii) dimensions between 5 cm×15 cm and 15 cm×30 cm; (iii) average pore diameter greater than 75 μm and less than 5 mm; (iv) fenestrations; (v) a suture pullout strength of the implant is between 10 gf, and 20 kgf; (vi) an endotoxin content of less than 20 EU per device, is sterile, and wherein the implant is packaged or (v) comprises struts having a diameter or width between 10 μm and 1 mm.

4. The implant of claim 1 wherein the sacrificial polymeric fibers, the non-sacrificial polymeric fibers or both the sacrificial and non-sacrificial polymeric fibers comprise poly-4-hydroxybutyrate or copolymer thereof.

5. The implant of claim 1, wherein the sacrificial polymeric fibers are less oriented than the non-sacrificial polymeric fibers, or the sacrificial polymeric fibers have lower-weight average molecular weights than the non-sacrificial polymeric fibers, or the sacrificial polymeric fibers yield before the non-sacrificial polymeric fibers when the implant is expanded.

6. The implant of claim 1, wherein:
   (a) the sacrificial polymeric fibers have one or more of the following properties: (i) an elongation to break of between 100% and 1,000%, (ii) a tensile strength between 50 MPa and 300 MPa, (iii) a tensile modulus between 70 MPa and 400 MPa and (iv) an average fiber diameter from 10 μm to 500 μm; and/or
   (b) the non-sacrificial polymeric fibers have one or more of the following properties: (i) an elongation to break of between 10% and 100%, (ii) a tensile strength between 301 and 1,300 MPa, (iii) a tensile modulus between 401 MPa and 1 GPa; and (iv) an average fiber diameter from 10 μm to 1 mm.

7. The implant of claim 1, wherein the implant is macroporous; has a strength retention three months after implantation in the body of at least 40% of its original tensile strength or burst strength; or is completely absorbed within 24 months of implantation in the body.

8. The implant of claim 1, wherein the implant is expandable when attached in the breast in the vicinity of a tissue expander, by inflation of the tissue expander, and wherein the implant is expandable over a period between the time of implantation and 6 months post-implantation.

9. The implant of claim 1, wherein the implant has been sterilized using ethylene oxide, gamma-irradiation or electron beam irradiation.

10. The implant of claim 1, wherein the non-sacrificial polymeric fibers zigzag between the two outer spaced and opposed face layers.

11. The implant of claim 1, wherein the non-sacrificial polymeric fibers have an accordion structure that can be expanded when the sacrificial polymeric fibers are stretched or degraded.

12. The implant of claim 1, wherein the implant expands when the sacrificial polymeric fibers are elongated or degraded.

13. The implant of claim 1, wherein the implant is knitted.

14. The implant of claim 1, wherein the sacrificial polymeric fibers have a smaller diameter than the non-sacrificial polymeric fibers.

15. The implant of claim 1, wherein the sacrificial polymeric fibers are broken by inflation of a tissue expander before the non-sacrificial polymeric fibers are broken.

16. The implant of claim 1 wherein the sacrificial polymeric fibers, the non-sacrificial polymeric fibers or both the sacrificial and non-sacrificial polymeric fibers comprise an absorbable polymer.

17. A method of using the implant of claim 1, wherein the implant is used for breast reconstruction, the method comprising the steps of: (i) implanting a tissue expander in the patient; (ii) implanting the implant in the vicinity of the tissue expander; (iii) expanding the tissue expander; (iv) removing the tissue expander; and (v) implanting a permanent breast implant in the patient.

18. The method of claim 17, wherein the permanent breast implant is implanted into a pocket created by the tissue expander and optionally, wherein the breast implant is a saline breast implant or a silicon breast implant.

19. The method of claim 18, wherein the patient has had a mastectomy.

20. The method of claim 18, wherein the pectoralis major muscle is mobilized, and the implant is sutured to the detached pectoralis major muscle edge to function as a pectoralis extender and form a sling to create a submuscular pocket for the tissue expander, and wherein the inferolateral portion of the tissue expander is covered by the implant.

21. A method of forming the implant of claim 1 comprising processing an unoriented or partially oriented absorbable polymer to form a lattice or mesh, wherein the lattice or mesh comprises the sacrificial polymeric fibers and the non-sacrificial polymeric fibers, wherein the sacrificial polymeric fibers degrade faster than the non-sacrificial polymeric fibers.

22. The method of claim 21, wherein:
   (a) the unoriented or partially oriented absorbable polymer has one or more of the following properties: (i) an elongation to break between 50% and 1,000%, (ii) a tensile strength between 50 MPa and 300 MPa, and (iii) a tensile modulus between 70 MPa and 400 MPa; or
   (b) the lattice or mesh has one or more of the following properties after expansion: (i) an elongation to break after expansion between 10% and 100%, (ii) a tensile strength after expansion between 301 and 1,300 MPa, and (iii) a tensile modulus between 401 MPa and 1 GPa.

23. The method of claim 21, wherein the lattice or mesh comprises poly-4-hydroxybutyrate or copolymer thereof.

24. The method of claim 23, wherein (a) the lattice is made of fibers comprising poly-4-hydroxybutyrate or copolymer thereof, or (b) the mesh is made of absorbable fibers, optionally, wherein the fibers are monofilament fibers, and optionally, wherein diameter of the fibers is between 10 µm and 1 mm.

25. The method of claim 21, wherein: (a) the implant is macro-porous, and optionally, has average pore diameters between diameters greater than 75 µm and less than 5 mm;
   (b) the implant has a thickness between 100 µm and 1 cm;
   (c) the implant has a suture pullout strength between 10 gf, and 20 kgf and/or (d) the implant has an endotoxin content of less than 20 endotoxin units.

26. The method of claim 21, wherein the implant is expanded using a tissue expander.

27. The method of claim 21, wherein the implant has one or more of the following properties: (i) the sacrificial polymeric fibers are less oriented than the non-sacrificial polymeric fibers, (ii) the sacrificial polymeric fibers have lower weight average molecular weights than the non-sacrificial polymeric fibers, (iii) the sacrificial polymeric fibers have smaller average diameters, widths, or other dimensions than the non-sacrificial polymeric fibers.

28. The method of claim 27, wherein:
   (a) the sacrificial polymeric fibers have one or more of the following properties: (i) an elongation to break of between 100% and 1,000%, (ii) a tensile strength between 50 MPa and 300 MPa, (iii) a tensile modulus between 70 MPa and 400 MPa;
   (b) the sacrificial polymeric fibers have an average diameter from 10 µm to 500 µm;
   (c) the non-sacrificial polymeric fibers have one or more of the following properties: (i) an elongation to break of between 10% and 100%, (ii) a tensile strength between 301 and 1,300 MPa, and (iii) a tensile modulus between 401 MPa and 1 GPa; and
   (d) the non-sacrificial polymeric fibers have an average diameter from 10 µm to 1 mm.

29. The method of claim 21, wherein the lattice or mesh comprises poly-4-hydroxybutyrate or copolymer thereof.

30. The method of claim 20, wherein mesh is made of monofilament or multifilament fibers preferably comprising poly-4-hydroxybutyrate or copolymer thereof.

31. The method of claim 30, comprising polymeric structs, wherein the width of the struts or diameter of the fibers is between 10 µm and 1 mm.

* * * * *

UNITED STATES PATENT AND TRADEMARK OFFICE
CERTIFICATE OF CORRECTION

| | |
|---|---|
| PATENT NO. | : 11,554,007 B2 |
| APPLICATION NO. | : 16/279378 |
| DATED | : January 17, 2023 |
| INVENTOR(S) | : Skander Limem et al. |

It is certified that error appears in the above-identified patent and that said Letters Patent is hereby corrected as shown below:

In the Specification

At Column 10, Line 6, replace "ILA" with --II.A--

At Column 10, Line 52, replace "ILA" with --II.A--

At Column 25, Line 6, replace "(p)" with --($\rho$)--

In the Claims

At Column 28, Claim 30, Line 35, replace "20" with --29--

Signed and Sealed this
Eleventh Day of April, 2023

Katherine Kelly Vidal
*Director of the United States Patent and Trademark Office*